(12) United States Patent
Takahashi et al.

(10) Patent No.: US 9,389,124 B2
(45) Date of Patent: Jul. 12, 2016

(54) TERAHERTZ ELECTROMAGNETIC WAVE GENERATOR, TERAHERTZ SPECTROMETER AND METHOD OF GENERATING TERAHERTZ ELECTROMAGNETIC WAVE

(71) Applicant: Panasonic Intellectual Property Management Co., Ltd., Osaka (JP)

(72) Inventors: Kohei Takahashi, Osaka (JP); Tsutomu Kanno, Kyoto (JP); Akihiro Sakai, Nara (JP); Yuka Yamada, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 104 days.

(21) Appl. No.: 14/539,229

(22) Filed: Nov. 12, 2014

(65) Prior Publication Data

US 2015/0069238 A1   Mar. 12, 2015

Related U.S. Application Data

(63) Continuation of application No. PCT/JP2014/000927, filed on Feb. 21, 2014.

(30) Foreign Application Priority Data

Mar. 18, 2013   (JP) ................................ 2013-054779

(51) Int. Cl.
*G01J 5/10* (2006.01)
*H01L 35/16* (2006.01)
(Continued)

(52) U.S. Cl.
CPC ................. *G01J 5/10* (2013.01); *G01J 3/2823* (2013.01); *G01N 21/3586* (2013.01); *G02F 1/353* (2013.01); *H01L 35/16* (2013.01); *G02F 2203/13* (2013.01)

(58) Field of Classification Search
USPC .................... 250/332, 338.1, 504 R; 359/326
See application file for complete search history.

(56) References Cited

U.S. PATENT DOCUMENTS 6,958,853 B1   10/2005   Arnone et al.
2003/0189235 A1*   10/2003   Watanabe .............. B82Y 10/00
257/432

(Continued)

FOREIGN PATENT DOCUMENTS

| JP | 2006-216799 A | 8/2006 |
| JP | 2008-177288 A | 7/2008 |
| WO | WO 01/23956 A2 | 4/2001 |
| WO | WO 2010/142313 A1 | 12/2010 |

OTHER PUBLICATIONS

International Search Report for corresponding International Application No. PCT/JP2014/000927 dated May 20, 2014.

(Continued)

*Primary Examiner* — Phillip A Johnston
*Assistant Examiner* — Hsien Tsai
(74) *Attorney, Agent, or Firm* — Renner, Otto, Boisselle & Sklar, LLP

(57) ABSTRACT

A terahertz electromagnetic wave generator according to the present disclosure includes: a substrate; a thermoelectric material layer which is supported by the substrate and which has a surface; and a pulsed laser light source system which locally heats the thermoelectric material layer with an edge of the surface of the thermoelectric material layer irradiated with pulsed light, thereby generating a terahertz electromagnetic wave from the thermoelectric material layer.

12 Claims, 30 Drawing Sheets

(51) Int. Cl.
  *G01N 21/3586* (2014.01)
  *G02F 1/35* (2006.01)
  *G01J 3/28* (2006.01)

(56) References Cited

U.S. PATENT DOCUMENTS

2004/0201076 A1* 10/2004 Shur .................... H01S 1/02
                                                    257/462
2012/0132832 A1*  5/2012 Dekorsy ............... H01S 1/02
                                                    250/504 R

OTHER PUBLICATIONS

Ferguson et al., "Materials for terahertz science and technology", Nature Materials, vol. 1, Sep. 2002, pp. 26-33.
Kai Liu et al., "Terahertz radiation from InAs induced by carrier diffusion and drift", Physical Review, B 73 (2006), pp. 155330-1-155330-6.
Co-pending U.S. Appl. No. 14/539,355, filed Nov. 12, 2014.
Co-pending U.S. Appl. No. 14/539,465, filed Nov. 12, 2014.

* cited by examiner n-TYPE THERMOELECTRIC MATERIAL p-TYPE THERMOELECTRIC MATERIAL

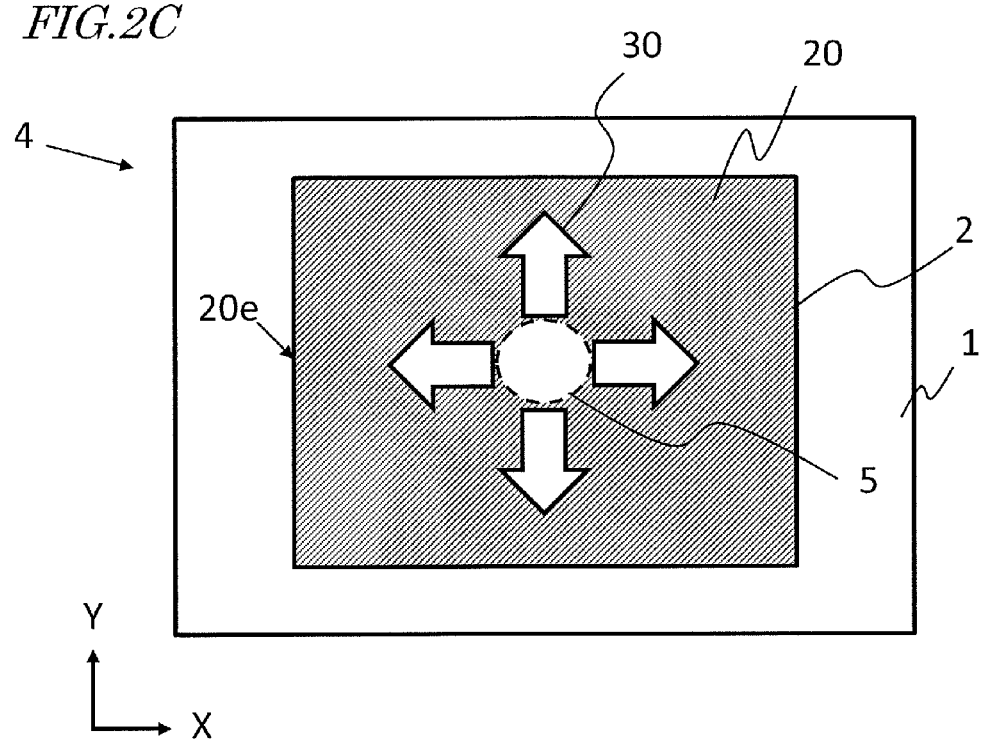

TERAHERTZ ELECTROMAGNETIC WAVE GENERATOR, TERAHERTZ SPECTROMETER AND METHOD OF GENERATING TERAHERTZ ELECTROMAGNETIC WAVE

This is a continuation of International Application No. PCT/JP2014/000927, with an international filing date of Feb. 21, 2014, which claims priority of Japanese Patent Application No. 2013-054779, filed on Mar. 18, 2013, the contents of which are hereby incorporated by reference.

BACKGROUND

1. Technical Field

The present application relates to a terahertz electromagnetic wave generator, a terahertz spectrometer, and a method of generating a terahertz electromagnetic wave.

2. Description of the Related Art

In this specification, the "terahertz electromagnetic wave" will refer herein to an electromagnetic wave, of which the frequency falls within the range of 0.1 THz to 100 THz. 1 THz (terahertz) is $1 \times 10^{12}$ (=the twelfth power of 10) Hz. Terahertz electromagnetic waves are now used in various fields including security, medical treatments, and nondestructive tests on electronic parts. Since there are excitation, vibration and rotation modes of various electronic materials, organic molecules and gas molecules in the terahertz electromagnetic wave frequency range, people have proposed that a terahertz electromagnetic wave be used as a sort of "fingerprint" to recognize a given material. On top of that, since a terahertz electromagnetic wave is safer than an X ray or any of various other electromagnetic waves, the terahertz electromagnetic wave can be used to make a medical diagnosis without doing harm on the body of a human subject.

As disclosed in Nature Mater. 1, 26, (2002), a photoconductor or a nonlinear optical crystal is used as a conventional terahertz electromagnetic wave generator. In any of those elements, a terahertz electromagnetic wave is generated by irradiating the element with a laser beam, of which the pulse width falls within the range of a few femtoseconds to several hundred femtoseconds (and which will be hereinafter referred to as a "femtosecond laser beam"). 1 femtosecond is $1 \times 10^{-15}$ (=the minus fifteenth power of 10) seconds. In a vacuum, an electromagnetic wave travels approximately 300 nm in one femtosecond.

Such a terahertz electromagnetic wave is generated by taking advantage of a so-called "dipole radiation" phenomenon in classical electromagnetism. That is to say, a variation in electric polarization or current in accelerated motion with time generates an electromagnetic wave at a frequency corresponding to the rate of that variation. Since a variation in polarization or current is induced in a few femtoseconds to several hundred femtoseconds (which depends on the pulse width of the laser beam) by being irradiated with a femtosecond laser beam, the electromagnetic wave generated by dipole radiation has a frequency falling within the terahertz range.

SUMMARY

According to a method of generating a terahertz electromagnetic wave using a photoconductor, a bias voltage needs to be applied to the photoconductor. That is why to generate a terahertz electromagnetic wave, not only a femtosecond laser diode but also an external voltage supply are needed. However, to use the terahertz electromagnetic wave technologies in a broader range of fields in practice, a method of generating a terahertz electromagnetic wave without using such an external voltage supply should be provided so that the technologies work in various operating environments.

According to a method of generating a terahertz electromagnetic wave using a nonlinear optical crystal, on the other hand, no external voltage supply is needed. However, since the second-order nonlinear optical effect is used, a femtosecond laser beam needs to be radiated precisely toward a predetermined crystal orientation of a nonlinear optical crystal. In addition, the phase matching condition needs to be satisfied, and therefore, the nonlinear optical crystal should be designed, shaped and controlled precisely enough.

The present disclosure provides a technique for generating a terahertz electromagnetic wave using a simpler configuration.

In one general aspect, a terahertz electromagnetic wave generator disclosed herein includes: a substrate; a thermoelectric material layer which is supported by the substrate and which has a surface; and a pulsed laser light source system which locally heats the thermoelectric material layer with an edge of the surface of the thermoelectric material layer irradiated with pulsed light, thereby generating a terahertz electromagnetic wave from the thermoelectric material layer.

In another aspect, a terahertz spectrometer disclosed herein includes: the terahertz electromagnetic wave generator described above; an optical system which irradiates an object with a terahertz electromagnetic wave that is generated by the terahertz electromagnetic wave generator; and a detector which detects the terahertz electromagnetic wave that is transmitted through, or reflected from, the object.

In another aspect, a method of generating a terahertz electromagnetic wave disclosed herein includes: (A) providing a thermoelectric material body; and (B) locally heating the thermoelectric material body by irradiating a portion of the thermoelectric material body with pulsed light. The step (B) includes: locally heating the thermoelectric material body so that an asymmetric heat distribution is formed in the thermoelectric material body; and producing thermal diffusion current in the portion of the thermoelectric material body that is heated locally, thereby generating a terahertz electromagnetic wave.

According to the present disclosure, by irradiating a thermoelectric material layer with a femtosecond laser beam, a macroscopic current can be induced, and a terahertz electromagnetic wave can be generated from this current.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 2C is a top view schematically illustrating how the terahertz electromagnetic wave generator 4 operates when a center portion of the surface 20 of the thermoelectric material layer 2 is irradiated with the femtosecond laser beam 5.

DETAILED DESCRIPTION

Figure 1A:
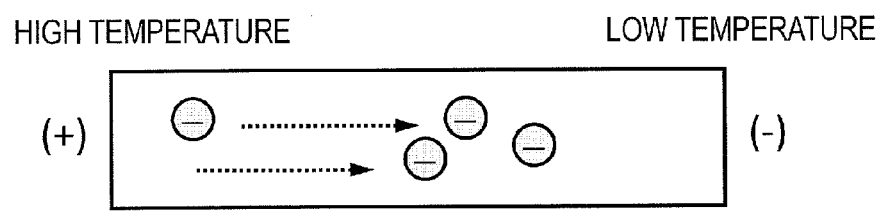
FIG. 1A illustrates how the Seebeck effect is produced.
Figure 1A:
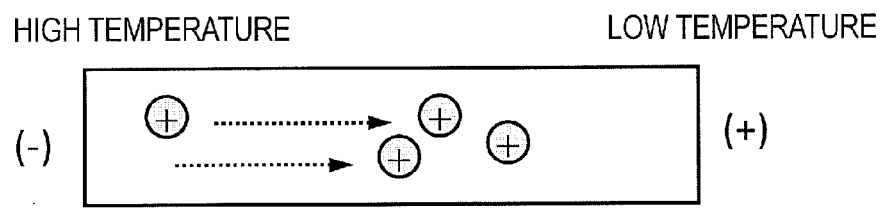

A terahertz electromagnetic wave generator according to the present disclosure uses the Seebeck effect to be expressed by a thermoelectric material. The Seebeck effect is a phenomenon that a difference in temperature in an object is directly converted to a voltage and is a kind of a thermoelectric effect. FIG. 1A schematically illustrates how the Seebeck effect is produced. In FIG. 1A, illustrated are an n-type thermoelectric material and a p-type thermoelectric material. In each of these materials, the temperature is higher at its left end than at its right end. In this case, in the n-type thermoelectric material, electrons that are majority carriers move (i.e., diffuse thermally) from the left at a relatively high temperature to the right at a relatively low temperature, thus generating a voltage. On the other hand, in the p-type thermoelectric material, holes that are majority carriers move (i.e., diffuse thermally) from the left at a relatively high temperature to the right at a relatively low temperature, thus generating a voltage. In both of these two materials, the majority carriers move in the same direction from a portion at the higher temperature toward a portion at the lower temperature. However, the polarity of the majority carriers of the n-type thermoelectric material is opposite from that of the majority carriers of the p-type thermoelectric material, and therefore, currents flow through the materials in mutually opposite directions.

In general, a thermoelectric material is a material which generates a voltage and current by producing a temperature gradient within the substance. According to the present disclosure, a temperature gradient is introduced into a thermoelectric material with a femtosecond laser beam, thereby producing current through the thermal diffusion. And by using that current, a terahertz electromagnetic wave is generated by dipole radiation. Nevertheless, if current has been induced symmetrically in a space, it can be said that no current has been produced macroscopically, and therefore, no terahertz electromagnetic wave is generated, either. On the other hand, if asymmetric current can be induced, then the current will flow in one direction macroscopically, and a terahertz electromagnetic wave can be generated by dipole radiation.

A terahertz electromagnetic wave generator according to the present disclosure includes: a substrate; a thermoelectric material layer which is supported by the substrate and which has a surface; and a pulsed laser light source system which locally heats the thermoelectric material layer with an edge of the surface of the thermoelectric material layer irradiated with pulsed light, thereby generating a terahertz electromagnetic wave from the thermoelectric material layer.

Embodiments of the present disclosure will now be described.

EMBODIMENTS

Figure 1B:
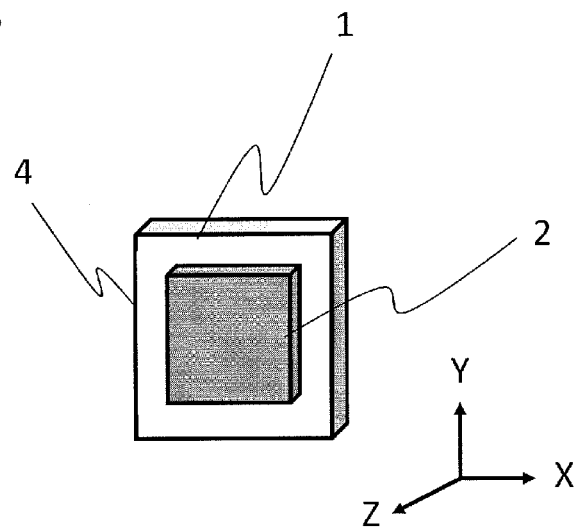
FIG. 1B is a perspective view illustrating a terahertz electromagnetic wave generator according to the present disclosure.

FIG. 1B is a perspective view illustrating a terahertz electromagnetic wave generator 4 as an embodiment of the present disclosure. As shown in FIG. 1B, the terahertz electromagnetic wave generator 4 for use in this embodiment includes a substrate 1 and a thermoelectric material layer 2 which is supported by the substrate 1. For your reference, XYZ coordinates represented by X, Y and Z axes that intersect with each other at right angles are shown in FIG. 1B. The substrate 1 illustrated in FIG. 1B has a flat plate shape. The principal surface of the substrate 1 is parallel to an XY plane and intersects with the Z axis at right angles.

Figure 1C:
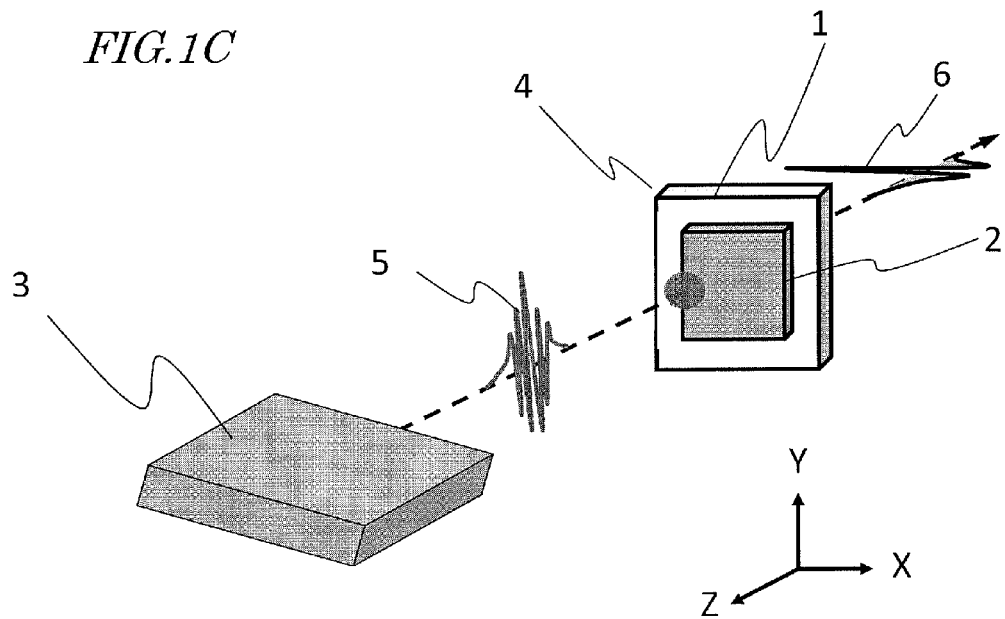
FIG. 1C is a schematic representation illustrating a terahertz electromagnetic wave generator according to the present disclosure.

FIG. 1C is a perspective view schematically illustrating an exemplary configuration for a terahertz electromagnetic wave generator according to an embodiment of the present disclosure. As shown in FIG. 1C, the terahertz electromagnetic wave generator of this embodiment includes a femtosecond laser light source 3 and a terahertz electromagnetic wave generator 4, which includes the thermoelectric material layer 2 supported by the substrate 1 as described above. The femtosecond laser light source 3 of this embodiment irradiates an edge of the thermoelectric material layer 2 of the terahertz electromagnetic wave generator 4 with a pulsed femtosecond laser beam 5. The femtosecond laser beam may have a pulse width of 1 femtosecond to 1 nanosecond, and typically has a pulse width falling within the range of 10 femtoseconds to 100 femtoseconds. Such a pulsed femtosecond laser beam can be radiated 1 to $10^8$ times per second. At the edge of the thermoelectric material layer 2 irradiated with such a pulsed femtosecond laser beam, the temperature rises in a short time (which is approximately as long as a laser beam radiation time) and current is thermally diffused due to the Seebeck effect and flows inward from the edge of the thermoelectric material layer 2. And based on this current, a terahertz electromagnetic wave 6 is radiated from around the edge of the thermoelectric material layer 2 into the surrounding space.

Figure 2A:
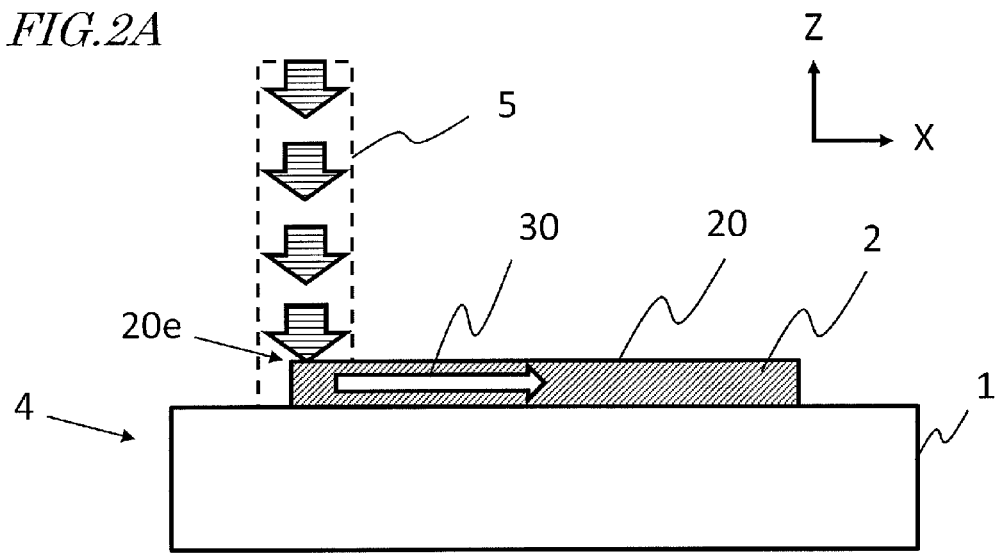
FIG. 2A is a cross-sectional view schematically illustrating how the terahertz electromagnetic wave generator 4 operates when a femtosecond laser beam 5 is incident on the generator 4.
Figure 2B:
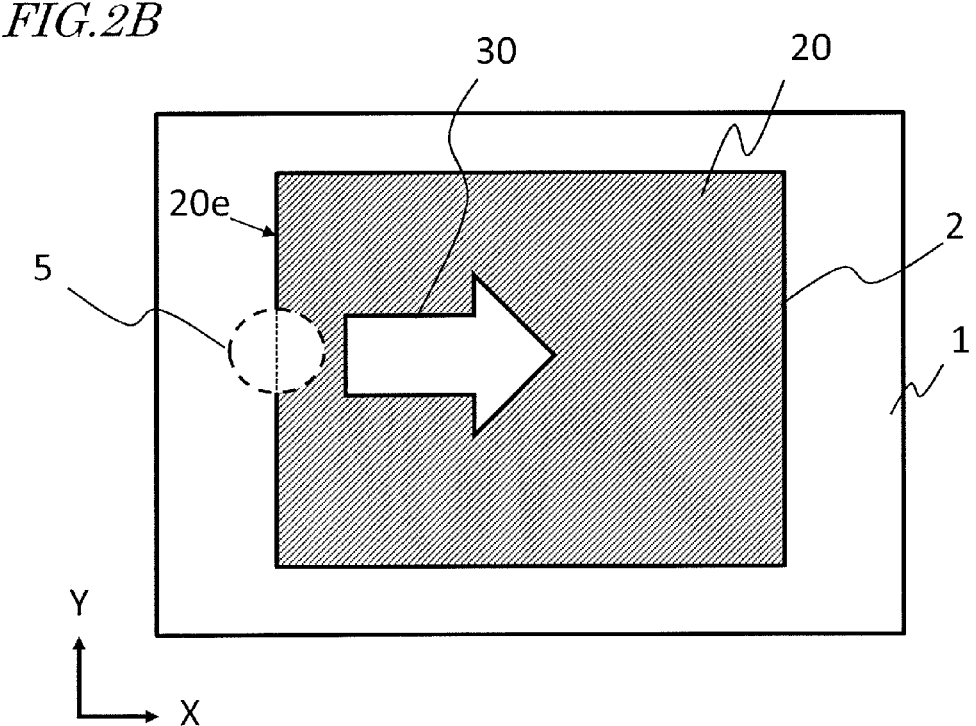
FIG. 2B is a top view schematically illustrating how the terahertz electromagnetic wave generator 4 operates when a femtosecond laser beam 5 is incident on the generator 4.

FIG. 2A is a cross-sectional view schematically illustrating how the terahertz electromagnetic wave generator 4 operates when a femtosecond laser beam 5 is incident on the generator 4, and FIG. 2B is a schematic top view of the generator 4. In the terahertz electromagnetic wave generator 4 shown in FIGS. 2A and 2B, the temperature rises steeply in a short time in its portion irradiated with the femtosecond laser beam 5, and a temperature gradient is produced generally in the direction indicated by the open arrow 30 in FIG. 2A. The temperature gradient has not only a component which is parallel to the X-axis direction shown in FIG. 2B but also a component in the Y-axis direction as well. However, in the temperature gradient, components in the +Y-axis and −Y-axis directions may be symmetric to each other, but components in the +X-axis and −X-axis directions are not symmetric to each other. Such a temperature gradient is produced by selectively raising the temperature of the thermoelectric material layer 2 only at its edge.

FIG. 2C is a top view schematically illustrating how the terahertz electromagnetic wave generator 4 operates when a center portion of the surface 20 of the thermoelectric material layer 2 is irradiated with the femtosecond laser beam 5. In this case, the spot of the femtosecond laser beam 5 does not cross the edge 20e of the surface 20 of the thermoelectric material layer 2, and the thermoelectric material layer 2 is irradiated with the femtosecond laser beam 5 fully. As schematically indicated by the arrows 30 in FIG. 2C, the temperature gradient produced in this case is isotropic within the XY plane.

The present inventors discovered via experiments that when the temperature gradient was isotropic within the XY plane, no terahertz electromagnetic wave was generated (as will be described later). In an embodiment of the present disclosure, on the other hand, a terahertz electromagnetic wave is generated. This is probably because thermally diffused current is produced asymmetrically within the XY plane as shown in FIG. 2B, for example.

According to this embodiment, if the spot radius of the femtosecond laser beam 5 is r, the radiation position of the femtosecond laser beam is adjusted so that the edge 20e of the surface 20 of the thermoelectric material layer 2 is located within the distance r from the center of the laser beam, and the surface edge of the thermoelectric material layer 2 is selectively heated by being irradiated with a pulsed laser beam. The spot radius r of the femtosecond laser beam 5 is defined to be the radius of an area where the beam intensity becomes equal to or greater than 1/e of the beam center intensity, where e is the base of natural logarithms and is represented by an approximate value of 2.7.

The femtosecond laser beam for use in this embodiment raises the temperature of the thermoelectric material layer 2 with pulses, and therefore, the wavelength of the laser beam is set to be a value falling within the range in which the laser beam is absorbed into the thermoelectric material layer 2. The wavelength range in which the laser beam is absorbed into the thermoelectric material layer 2 may vary according to the type of the thermoelectric material that forms the thermoelectric material layer 2.

In the terahertz electromagnetic wave generator of the present disclosure, the thermally diffused current produced by the Seebeck effect becomes the source of a terahertz electromagnetic wave, and therefore, it does not matter whether the material of the thermoelectric material layer 2 is an n-type material or a p-type one. The thermoelectric material layer 2 may be made of a material with a large Seebeck coefficient and a high degree of electrical conductivity. Examples of thermoelectric materials which may be used to make the thermoelectric material layer 2 include single-element thermoelectric materials such as Bi and Sb, alloy-based thermoelectric materials such as BiTe, PbTe and SiGe based materials, and oxide-based thermoelectric materials such as $Ca_xCoO_2$, $Na_xCoO_2$, and $SrTiO_3$. In this description, the "thermoelectric material" refers herein to a material with a Seebeck coefficient, of which the absolute value is equal to or greater than 30 μV/K, and an electrical resistivity of 10 mΩcm or less. Such a thermoelectric material may be either crystalline or amorphous.

The substrate 1 of this embodiment is made of a material which can transmit the terahertz electromagnetic wave generated and may be made of a dielectric material, for example. Examples of dielectric materials which may be used to make the substrate 1 include $SiO_2$, $Al_2O_3$, MgO, Si and LSAT. Not the entire substrate 1 has to be made of the same material, and the substrate 1 does not have to have a uniform thickness, either. The principal surface of the substrate 1 is typically flat but may have some unevenness, too. The function to be performed by the substrate 1 is to support the thermoelectric material layer 2. As long as the substrate 1 can perform this function, the substrate 1 may have any of various forms.

In the terahertz electromagnetic wave generator 4 of the present disclosure, the thermoelectric material layer 2 may have a thickness at which 50% or more of the terahertz electromagnetic wave generated can be transmitted. In the area where the terahertz electromagnetic wave is generated, the thickness of the thermoelectric material layer 2 may be set to fall within the range of 10 nm to 1000 nm (=1 μm), for example. The thermoelectric material layer 2 may be formed by any method, which may be a sputtering process, an evaporation process, a laser ablation process, a vapor deposition process such as chemical vapor deposition, a liquid phase deposition process, or any of various other methods. The thermoelectric material layer 2 does not have to be deposited directly on the principal surface of the substrate 1. Alternatively, the thermoelectric material layer 2 may be deposited on another substrate and then transferred onto the principal surface of the substrate 1.

Figure 2D:
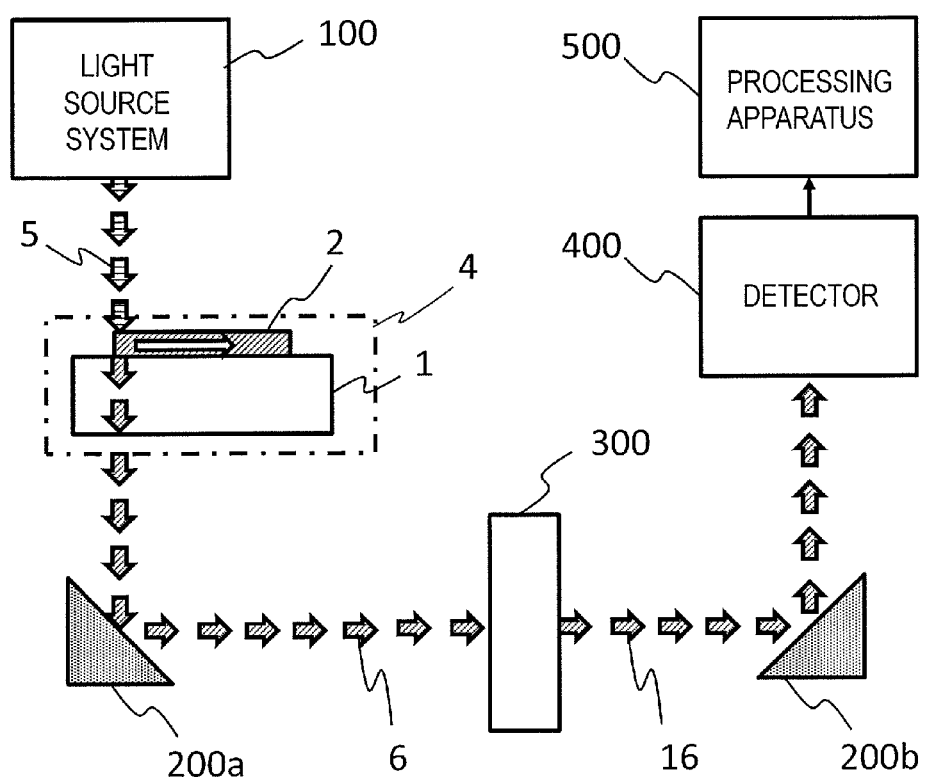
FIG. 2D illustrates an exemplary configuration for a terahertz spectrometer according to an embodiment of the present disclosure.

FIG. 2D illustrates an exemplary configuration for a terahertz spectrometer according to an embodiment of the present disclosure. This spectrometer includes a light source system 100 which emits the femtosecond laser beam 5, the terahertz electromagnetic wave generator 4 of the present disclosure, an optical system (including mirrors 200a and 200b) which irradiates an object (sample 300) with the terahertz electromagnetic wave 6 generated by the terahertz electromagnetic wave generator 4, and a detector 400 which detects the terahertz electromagnetic wave 16 that is transmitted through the sample 300. Optionally, this terahertz spectrometer may further include a processing apparatus 500 which generates an image representing a terahertz electromagnetic wave with a particular wavelength based on the output of the detector 400.

Figure 2E:
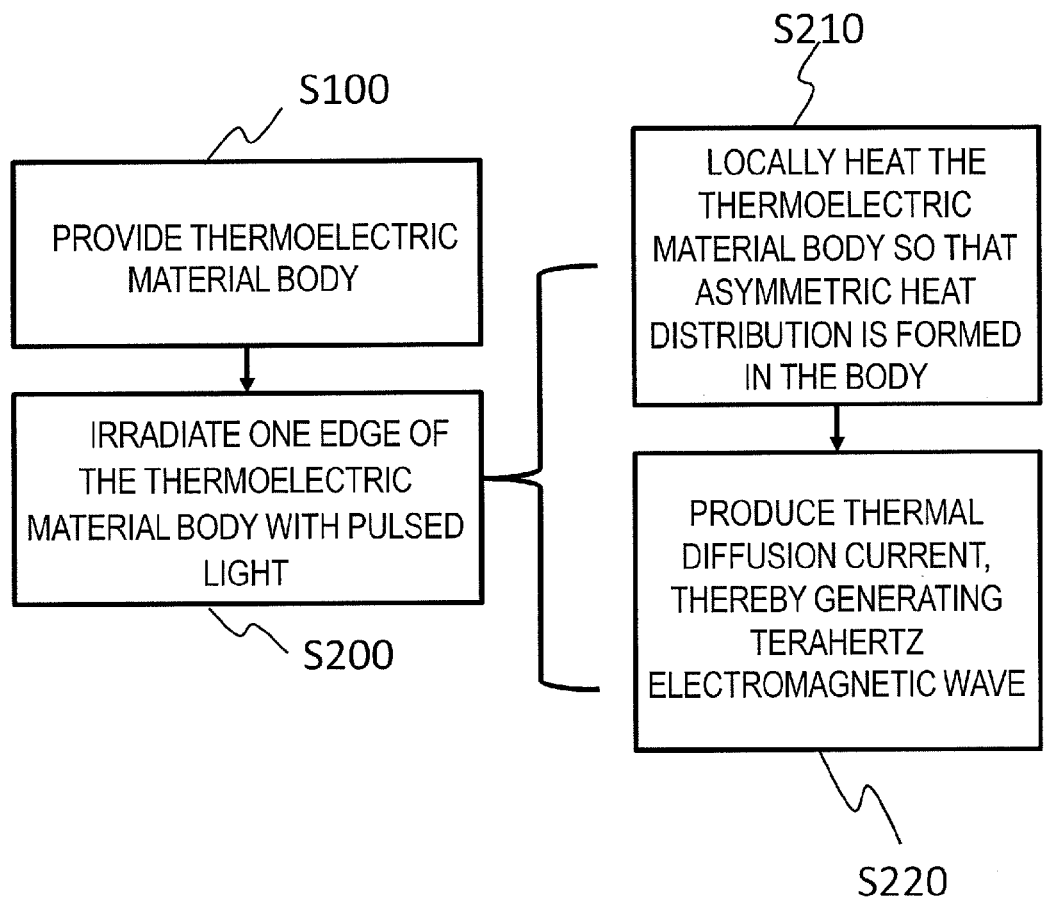
FIG. 2E is a flowchart showing the procedure of generating a terahertz electromagnetic wave.

As shown in FIG. 2E, a method of generating a terahertz electromagnetic wave according to the present disclosure includes the step S100 of providing a thermoelectric material body and the step S200 of locally heating the thermoelectric material body by irradiating an edge of the thermoelectric material body with pulsed light (e.g., the femtosecond laser beam). This step S200 includes the step S210 of locally heating the thermoelectric material body so that an asymmetric heat distribution is formed in the thermoelectric material body, and the step S220 of producing thermal diffusion current in the portion of the thermoelectric material body that is heated locally, thereby generating a terahertz electromagnetic wave.

The thermoelectric material layer 2 for use in this embodiment does not have to have the shape shown in FIGS. 2A and 2B. Alternatively, the thermoelectric material layer 2 may also be patterned by a known method to have any other shape. For example, the thermoelectric material layer 2 may have a linear pattern, a bent curved pattern or a curvilinear pattern or may also have a single or a plurality of holes. The thermoelectric material layer 2 may be divided into a plurality of portions on the single substrate 1 or may cover the principal surface of the substrate 1 entirely. Optionally, the thermoelectric material layer 2 may be partially extended out of the principal surface of the substrate 1. The thermoelectric material layer 2 may also be a nanowire layer. The surface of the thermoelectric material layer 2 does not have to be flat and its thickness does not have to be uniform within the plane, either.

Figure 2F:
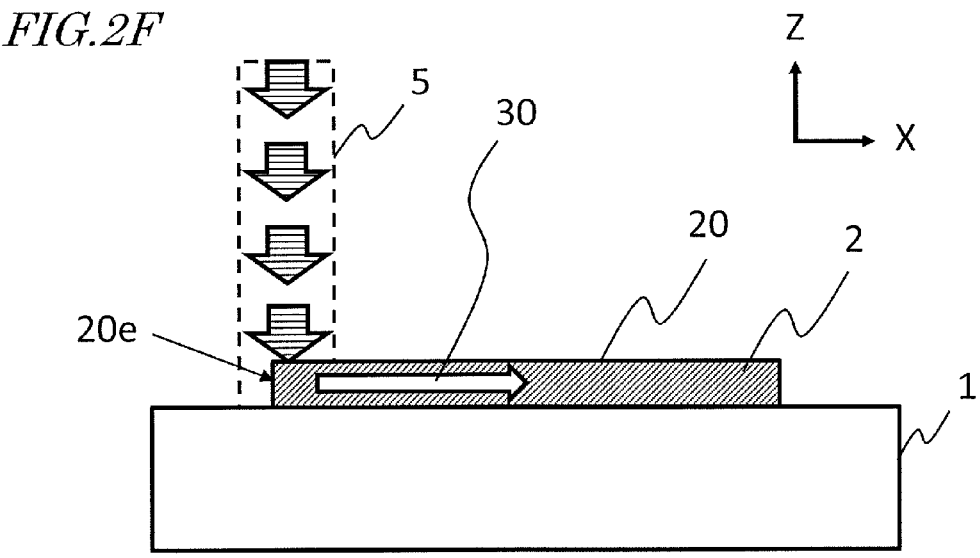
FIG. 2F is a cross-sectional view schematically illustrating a terahertz electromagnetic wave generator 4 with a thermoelectric material layer 2 which has been patterned into a linear shape.
Figure 2G:
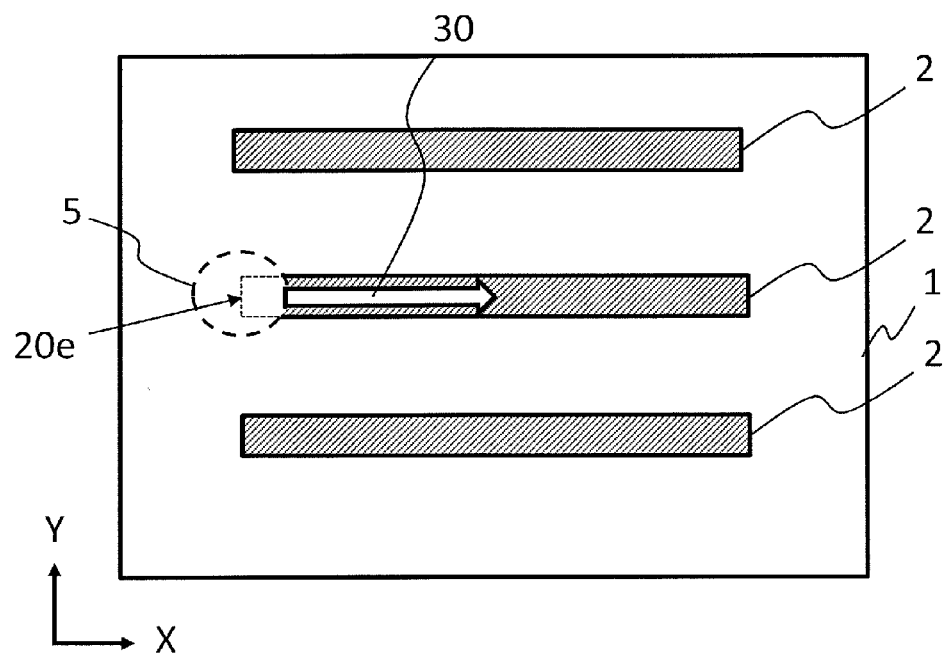
FIG. 2G is a top view schematically illustrating a terahertz electromagnetic wave generator 4 with a thermoelectric material layer 2 which has been patterned into a linear shape.

FIG. 2F is a cross-sectional view schematically illustrating a terahertz electromagnetic wave generator 4 with a thermoelectric material layer 2 which has been patterned into a linear shape, and FIG. 2G is a schematic top view thereof. In the terahertz electromagnetic wave generator 4 illustrated in FIGS. 2F and 2G, an edge 20e of the surface 20 of the thermoelectric material layer 2 that is supported on the substrate 1 is also irradiated with a femtosecond laser beam 5. In the example illustrated in FIGS. 2F and 2G, one of the three linear portions into which the thermoelectric material layer 2 has been patterned has one of its edges irradiated with the femtosecond laser beam 5.

Figure 2H:
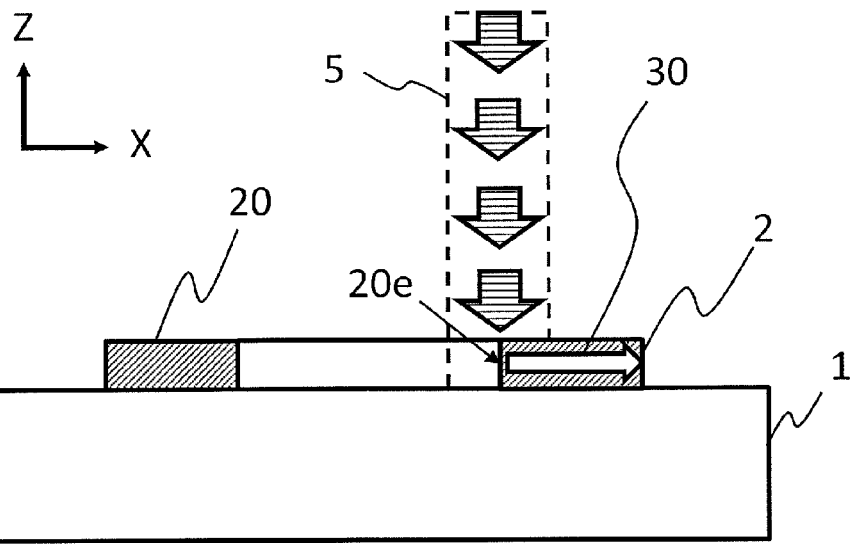
FIG. 2H is a cross-sectional view schematically illustrating a terahertz electromagnetic wave generator 4 including a thermoelectric material layer 2 with a hole.
Figure 2I:
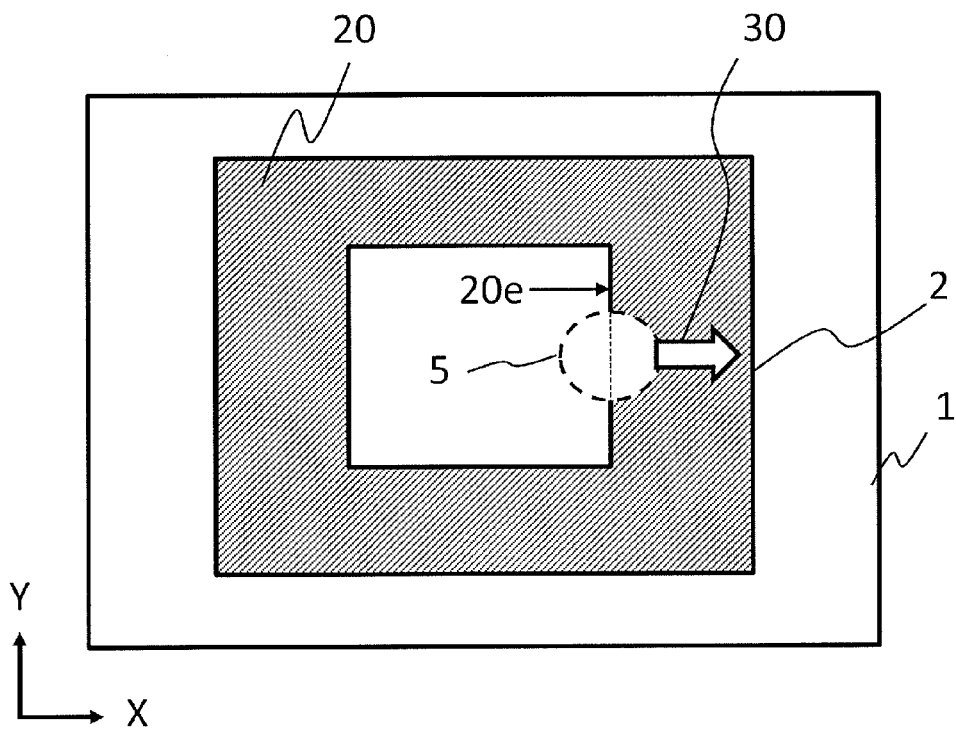
FIG. 2I is a top view schematically illustrating a terahertz electromagnetic wave generator 4 including a thermoelectric material layer 2 with a hole.

FIG. 2H is a cross-sectional view schematically illustrating a terahertz electromagnetic wave generator 4 including a thermoelectric material layer 2 with a hole, and FIG. 2I is a schematic top view thereof. In the terahertz electromagnetic wave generator 4 illustrated in FIGS. 2H and 2I, an edge 20e of the surface 20 of the thermoelectric material layer 2 is also irradiated with a femtosecond laser beam 5. In the example illustrated in FIGS. 2H and 2I, the edge 20e of the surface 20 is a portion of the outer periphery of the hole.

The following are some specific examples of the present disclosure.

EXAMPLE 1

An element which used Bi as a thermoelectric material and $SiO_2$ as a substrate material, respectively, was fabricated by the following method. Bi is an n-type thermoelectric material and had a Seebeck coefficient of −75 μV/K and an electrical resistivity of 0.1 mΩcm. On the other hand, $SiO_2$ is an insulator, not a thermoelectric material.

A Bi layer was deposited by evaporation process to a thickness of 50 nm on an $SiO_2$ substrate (10 mm×10 mm×0.5 mm). The evaporation process was carried out without heating the $SiO_2$ substrate after the film deposition chamber had been evacuated to a pressure of $1.0 \times 10^{-3}$ Pa or less. When the Bi layer was deposited, the principal surface of the $SiO_2$ substrate was covered with a metallic mask so that only a portion of the principal surface of the $SiO_2$ substrate would be coated with the Bi layer. In this manner, a terahertz electromagnetic wave generator with the structure shown in FIG. 1B (i.e., comprised of a thermoelectric material (Bi) and an insulator ($SiO_2$)) was fabricated. While the $SiO_2$ substrate had an area of 10 mm×10 mm, the Bi layer deposited on the substrate had an area of 1 mm×1 mm.

As the femtosecond laser light source to heat the terahertz electromagnetic wave generator, a Ti: Sapphire laser diode with a wavelength of 800 nm, a pulse width of 100 fs and a pulse rate of 80 MHz was used.

Figure 3A:
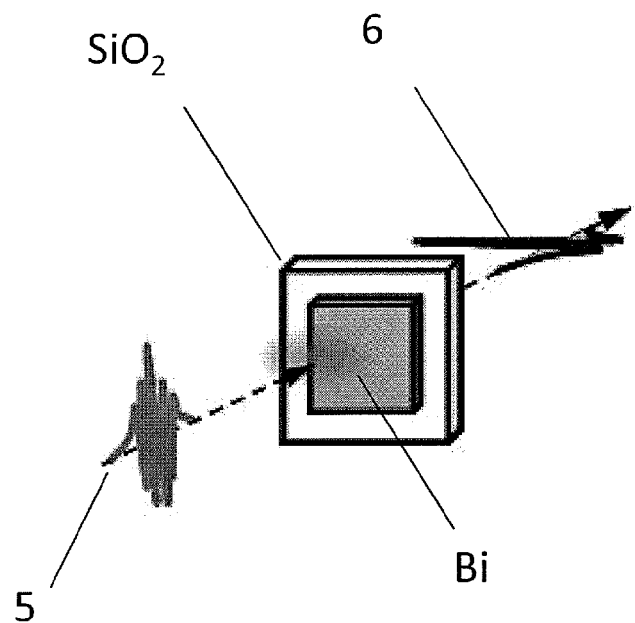
FIG. 3A is a perspective view illustrating a situation where a terahertz electromagnetic wave generator comprised of Bi and $SiO_2$ is arranged so that a right half of the area irradiated with a laser beam will be Bi and a left half of that area will be $SiO_2$.
Figure 3B:
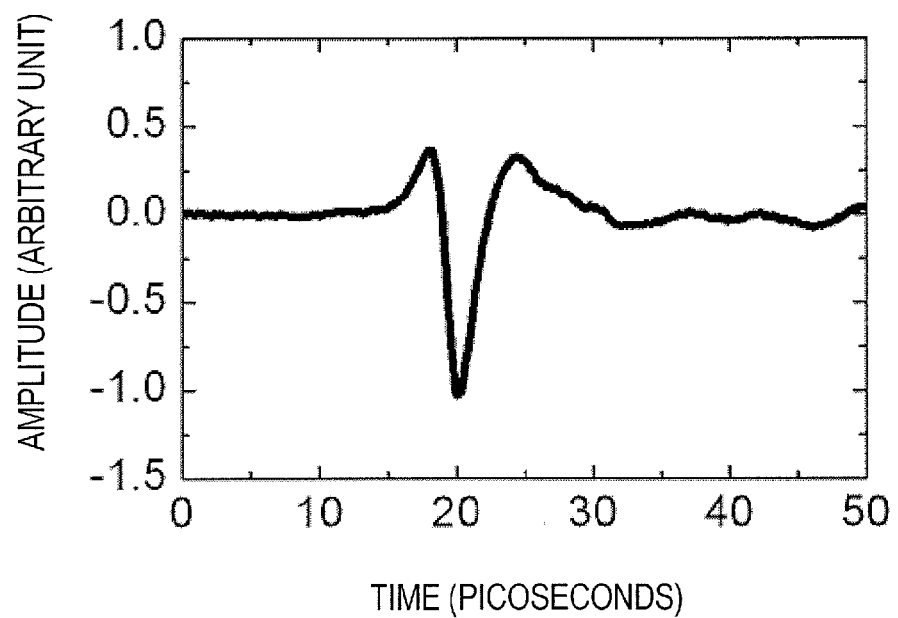
FIG. 3B is a graph showing the time domain waveform of a terahertz electromagnetic wave generated in such a situation where the terahertz electromagnetic wave generator comprised of Bi and $SiO_2$ was irradiated with a femtosecond laser beam and was arranged so that a right half of the area irradiated with the laser beam would be Bi and a left half of that area would be $SiO_2$.
Figure 4:
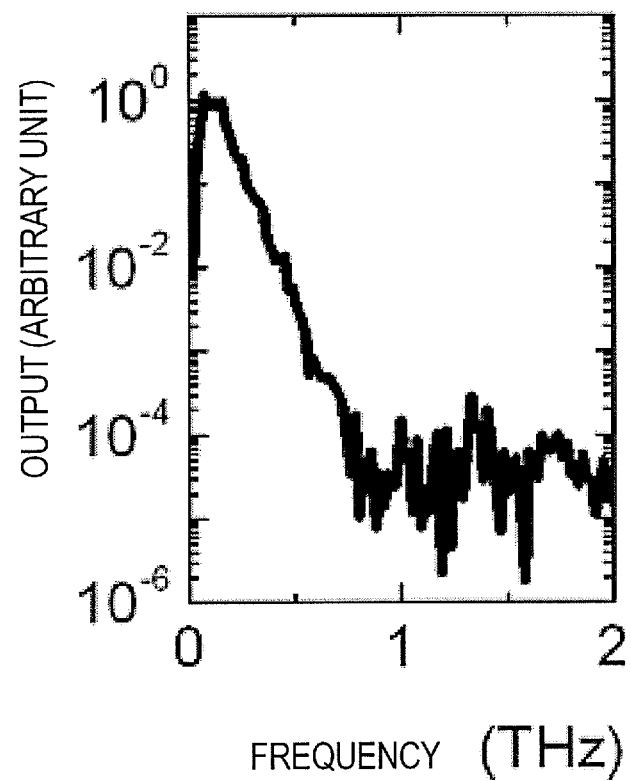
FIG. 4 is a graph showing the power spectrum of the terahertz electromagnetic wave shown in FIG. 3B.

With respect to the terahertz electromagnetic wave generator thus fabricated, one edge of the Bi layer was irradiated with a femtosecond laser beam that had been condensed to 100 μm (=2r), thereby measuring the time domain waveform of the terahertz electromagnetic wave. In this case, adjustment was made so that the center of the laser beam would be located on one edge of the Bi layer. First of all, the terahertz electromagnetic wave generator was irradiated with the femtosecond laser beam so that a right half of the area irradiated with the laser beam would be Bi and a left half of that area would be $SiO_2$ as shown in FIG. 3A. The time domain waveform of the terahertz electromagnetic wave generated in such a situation is shown in FIG. 3B. As can be seen from the time domain waveform of the terahertz electromagnetic wave shown in FIG. 3B, a pulse wave with a negative peak intensity was generated at around 20 ps (picoseconds). FIG. 4 shows a power spectrum obtained by subjecting this time domain waveform to a Fourier transform. The electromagnetic wave generated had a frequency range of about 0.1 THz to about 1 THz. Thus, it was confirmed that a terahertz electromagnetic wave had been generated.

Figure 5A:
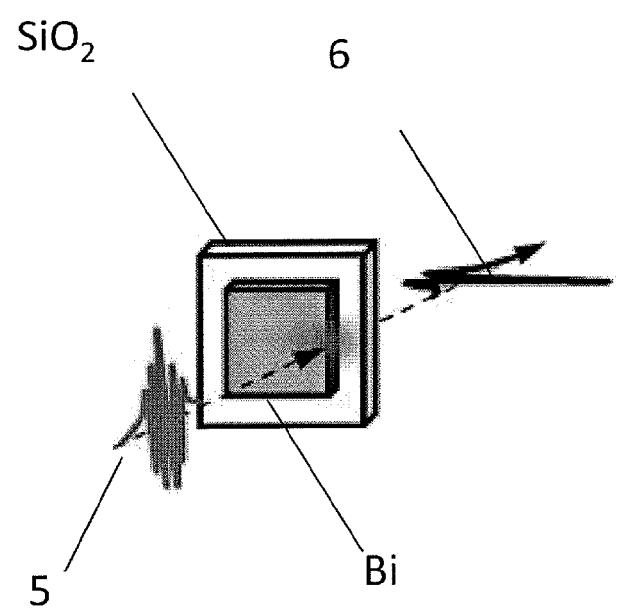
FIG. 5A is a perspective view illustrating a situation where a terahertz electromagnetic wave generator comprised of Bi and $SiO_2$ is arranged so that a left half of the area irradiated with a laser beam will be Bi and a right half of that area will be $SiO_2$.
Figure 5B:
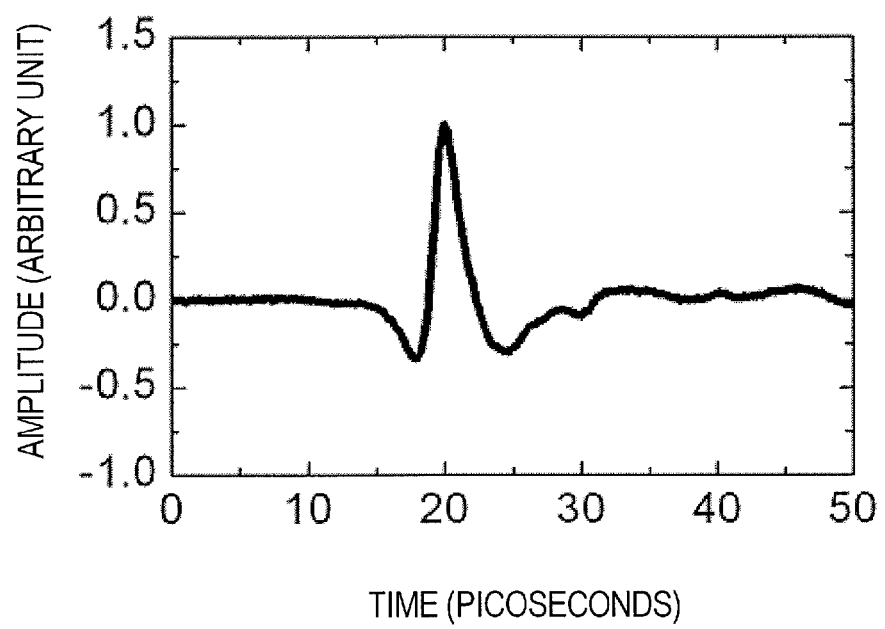
FIG. 5B is a graph showing the time domain waveform of a terahertz electromagnetic wave generated in such a situation where the terahertz electromagnetic wave generator comprised of Bi and $SiO_2$ was irradiated with a femtosecond laser beam and was arranged so that a left half of the area irradiated with the laser beam would be Bi and a right half of that area would be $SiO_2$.
Figure 6:
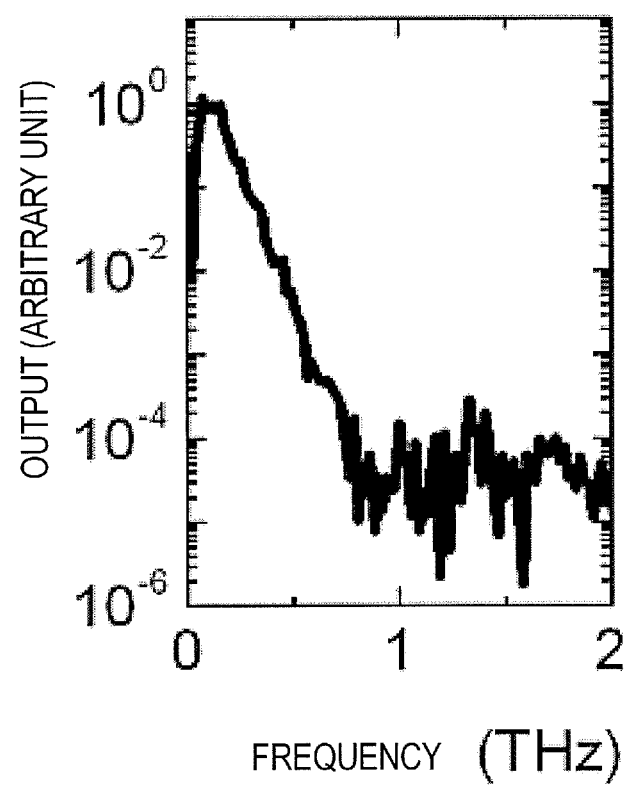
FIG. 6 is a graph showing the power spectrum of the terahertz electromagnetic wave shown in FIG. 3B.

Next, the terahertz electromagnetic wave generator was irradiated with the femtosecond laser beam so that a right half of the area irradiated with the laser beam would be $SiO_2$ and a left half of that area would be Bi as shown in FIG. 5A. The time domain waveform of the terahertz electromagnetic wave generated in such a situation is shown in FIG. 5B. As can be seen from the time domain waveform of the terahertz electromagnetic wave shown in FIG. 5B, a pulse wave with a positive peak intensity was generated at around 20 ps (picoseconds). FIG. 6 shows a power spectrum obtained by subjecting this time domain waveform to a Fourier transform. The electromagnetic wave generated had a frequency range of about 0.1 THz to about 1 THz. Thus, it was confirmed that a terahertz electromagnetic wave had been generated.

As can be seen from these results, the electric field polarity of the terahertz electromagnetic wave (i.e., whether the maximum peak of the time waveform is positive or negative) inverted depending on whether the terahertz electromagnetic wave had been generated so that a right half of the area irradiated with the laser beam would be Bi and a left half of that area would be $SiO_2$ as shown in FIG. 3A or that a right half of the area irradiated with the laser beam would be $SiO_2$ and a left half of that area would be Bi as shown in FIG. 5A. The electric field polarity of the terahertz electromagnetic wave is determined by the direction of current to be its source. That is why if the electric field polarity of the terahertz electromagnetic wave observed in FIG. 3B was inverse of that of the terahertz electromagnetic wave observed in FIG. 5B, then it means that the direction of current to be induced changed depending on whether Bi was located on the left half of the area irradiated with the laser beam or on the right half thereof. In fact, if the terahertz electromagnetic wave generator is irradiated with the femtosecond laser beam so that a right half of the area irradiated with the laser beam will be Bi and a left half of that area will be $SiO_2$ as shown in FIG. 3A, electrons heated within Bi will diffuse to the left, and therefore, current will flow to the right. On the other hand, if the terahertz electromagnetic wave generator is irradiated with the femtosecond laser beam so that a right half of the area irradiated with the laser beam will be $SiO_2$ and a left half of that area will be Bi as shown in FIG. 5A, electrons heated within Bi will diffuse to the right, and therefore, current will flow to the left. Since $SiO_2$ is an insulator, no current will flow through $SiO_2$ due to thermal diffusion.

Thus it can be understood why the polarity of the terahertz electromagnetic wave observed in FIG. 3B was inverse of that of the terahertz electromagnetic wave observed in FIG. 5B. And it can also be seen that the current generated in Bi that is a thermoelectric material becomes the source of a terahertz electromagnetic wave.

Figure 7:
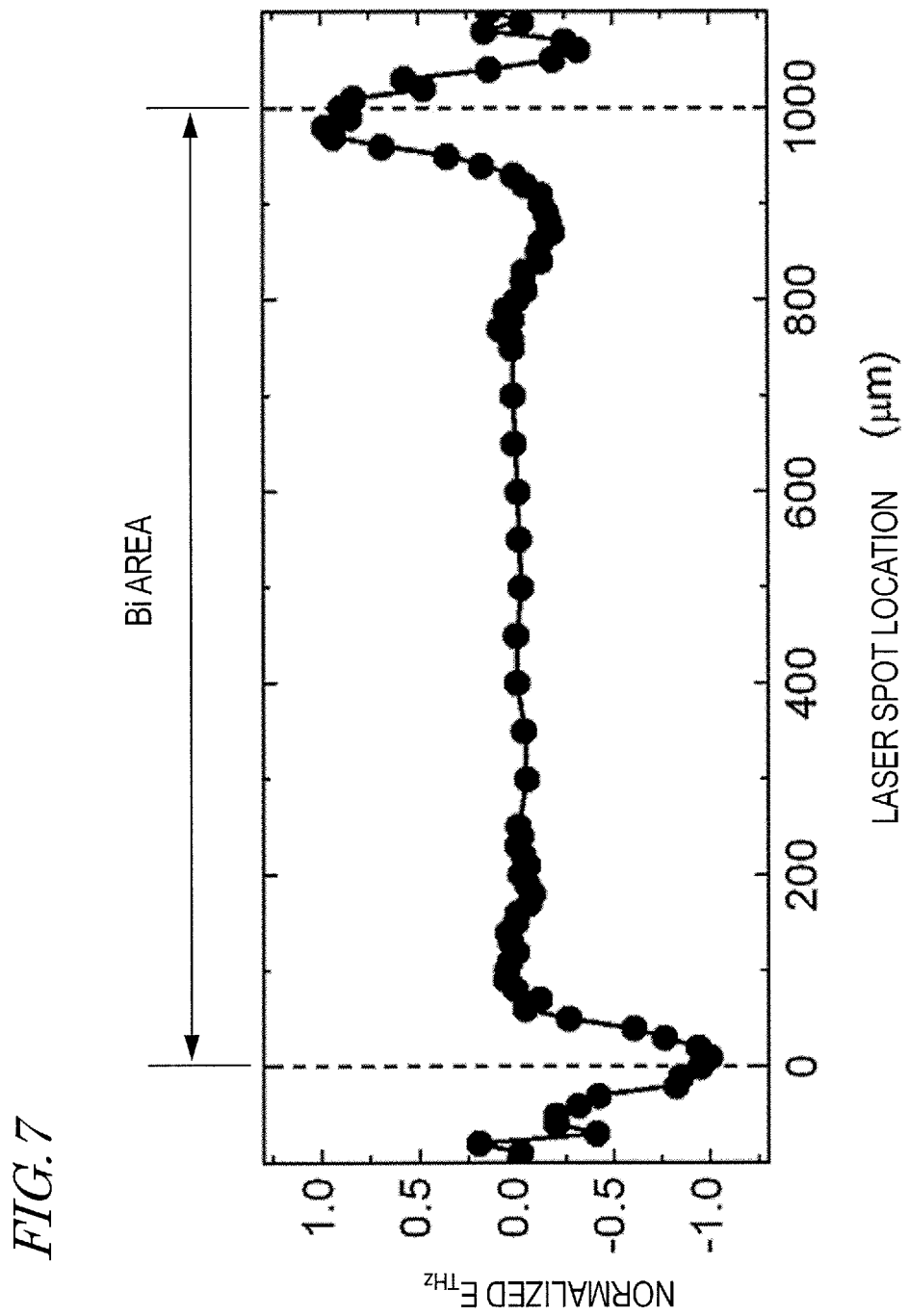
FIG. 7 is a graph showing a variation in the peak intensity of a terahertz electromagnetic wave that a terahertz electromagnetic wave generator comprised of Bi and $SiO_2$ generated when the area irradiated with a femtosecond laser beam was scanned one-dimensionally.

Next, a variation in the peak intensity of the terahertz electromagnetic wave generated was traced by scanning the area irradiated with the femtosecond laser beam from the $SiO_2$ side toward the Bi side. In this case, the femtosecond laser beam had a beam diameter (=2r) of 100 μm. The results are shown in FIG. 7. When the laser beam spot was located completely within the $SiO_2$ area, no terahertz electromagnetic wave was generated. However, when the laser beam was incident on an edge of the Bi layer, the peak intensity of the terahertz electromagnetic wave started to rise. And when the center of the laser beam spot was located in the vicinity of an edge of the Bi layer, the peak intensity of the terahertz electromagnetic wave reached its maximum value. As the laser beam spot was further shifted toward the Bi side, the peak intensity of the terahertz electromagnetic wave started to decrease. And when the laser beam spot entered the Bi area completely, no terahertz electromagnetic wave was observed anymore. However, when the laser beam spot was shifted to reach the opposite edge of the Bi layer, a terahertz electromagnetic wave was observed again. These results reveal that to generate a terahertz electromagnetic wave, it is important that an edge of the thermoelectric material layer falls within the area irradiated with the laser beam.

EXAMPLE 2

An element which used p-type $Bi_2Te_3$ as a thermoelectric material and $SiO_2$ as a substrate material, respectively, was fabricated by the following method. $Bi_2Te_3$ had a Seebeck coefficient of +210 μV/K and an electrical resistivity of 1 mΩcm. On the other hand, $SiO_2$ is an insulator, not a thermoelectric material.

A $Bi_2Te_3$ layer was deposited by evaporation process to a thickness of 50 nm on an $SiO_2$ substrate (10 mm×10 mm×0.5 mm). The evaporation process was carried out without heating the $SiO_2$ substrate after the film deposition chamber had been evacuated to a pressure of $1.0×10^{-3}$ Pa or less. When the $Bi_2Te_3$ layer was deposited, the principal surface of the $SiO_2$ substrate was covered with a metallic mask so that only a portion of the principal surface of the $SiO_2$ substrate would be coated with the $Bi_2Te_3$ layer. In this manner, a terahertz electromagnetic wave generator with the structure shown in FIG. 1B (i.e., comprised of a thermoelectric material ($Bi_2Te_3$) and an insulator ($SiO_2$)) was fabricated. While the $SiO_2$ substrate had an area of 10 mm×10 mm, the $Bi_2Ti_3$ layer deposited on the substrate had an area of 1 mm×1 mm.

As a femtosecond laser diode to heat the terahertz electromagnetic wave generator, a Ti: Sapphire laser diode with a wavelength of 800 nm, a pulse width of 100 fs and a pulse rate of 80 MHz was used.

With respect to the terahertz electromagnetic wave generator thus fabricated, one edge of the $Bi_2Te_3$ layer was irradiated with a femtosecond laser beam that had been condensed to 100 μm (=2r), thereby measuring the time domain waveform of the terahertz electromagnetic wave. In this case, adjustment was made so that the center of the laser beam would be located on one edge of the $Bi_2Ti_3$ layer.

Figure 8A:
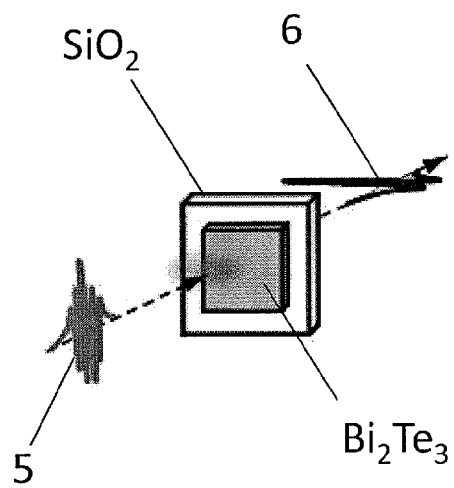
FIG. 8A is a perspective view illustrating a situation where a terahertz electromagnetic wave generator comprised of $Bi_2O_3$ and $SiO_2$ is arranged so that a right half of the area irradiated with a laser beam will be $Bi_2O_3$ and a left half of that area will be $SiO_2$.
Figure 8B:
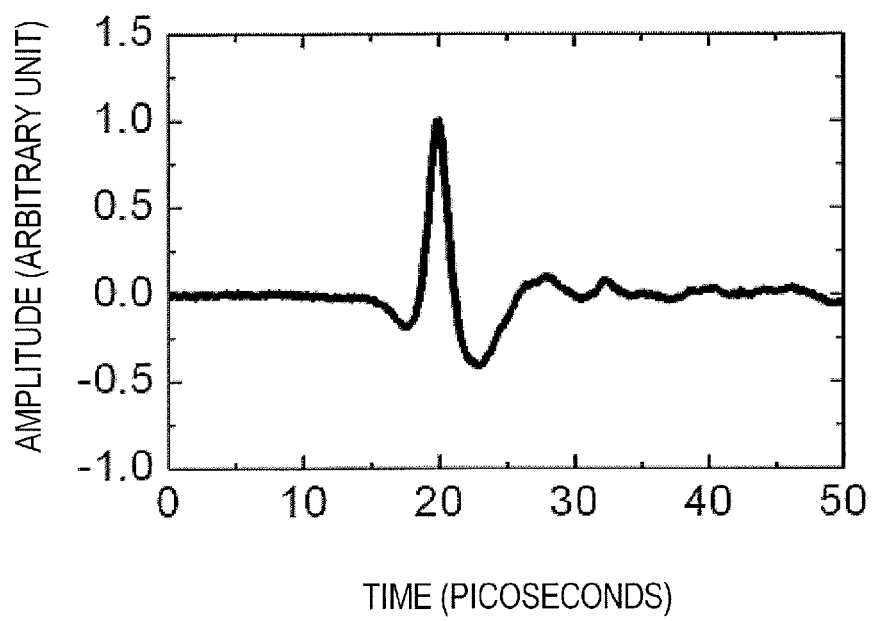
FIG. 8B is a graph showing the time domain waveform of a terahertz electromagnetic wave generated in such a situation where the terahertz electromagnetic wave generator comprised of $Bi_2O_3$ and $SiO_2$ was irradiated with a femtosecond laser beam and was arranged so that a right half of the area irradiated with the laser beam would be $Bi_2O_3$ and a left half of that area would be $SiO_2$.
Figure 9:
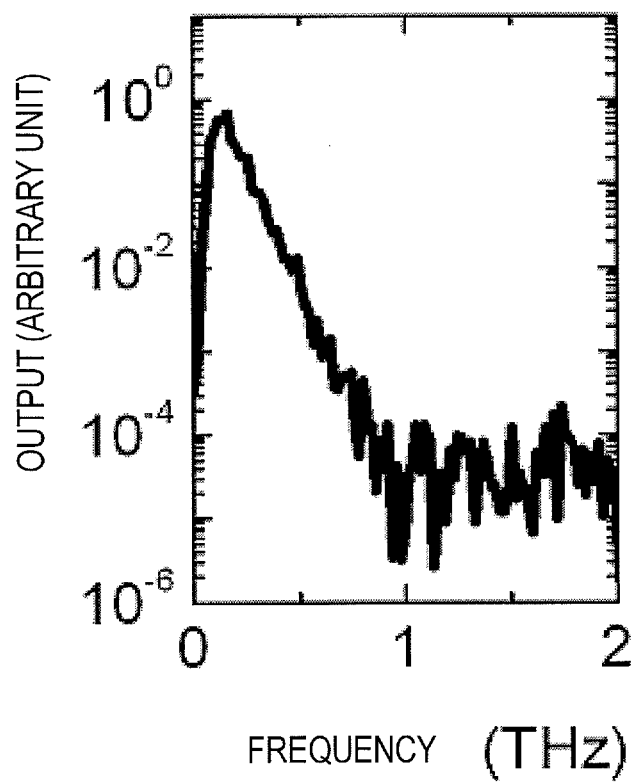
FIG. 9 is a graph showing the power spectrum of the terahertz electromagnetic wave shown in FIG. 8B.

First of all, the terahertz electromagnetic wave generator was irradiated with the femtosecond laser beam so that a right half of the area irradiated with the laser beam would be $Bi_2Te_3$ and a left half of that area would be $SiO_2$ as shown in FIG. 8A. The time domain waveform of the terahertz electromagnetic wave generated in such a situation is shown in FIG. 8B. As can be seen from the time domain waveform of the terahertz electromagnetic wave shown in FIG. 8B, a pulse wave with a positive peak intensity was generated at around 20 ps. FIG. 9 shows a power spectrum obtained by subjecting this time domain waveform to a Fourier transform. The electromagnetic wave generated had a frequency range of about 0.1 THz to about 1 THz. Thus, it was confirmed that a terahertz electromagnetic wave had been generated.

Figure 10A:
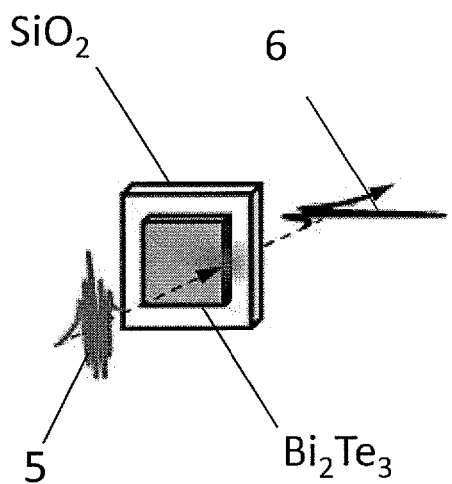
FIG. 10A is a perspective view illustrating a situation where a terahertz electromagnetic wave generator comprised of $Bi_2O_3$ and $SiO_2$ is arranged so that a left half of the area irradiated with a laser beam will be $Bi_2O_3$ and a right half of that area will be $SiO_2$.
Figure 10B:
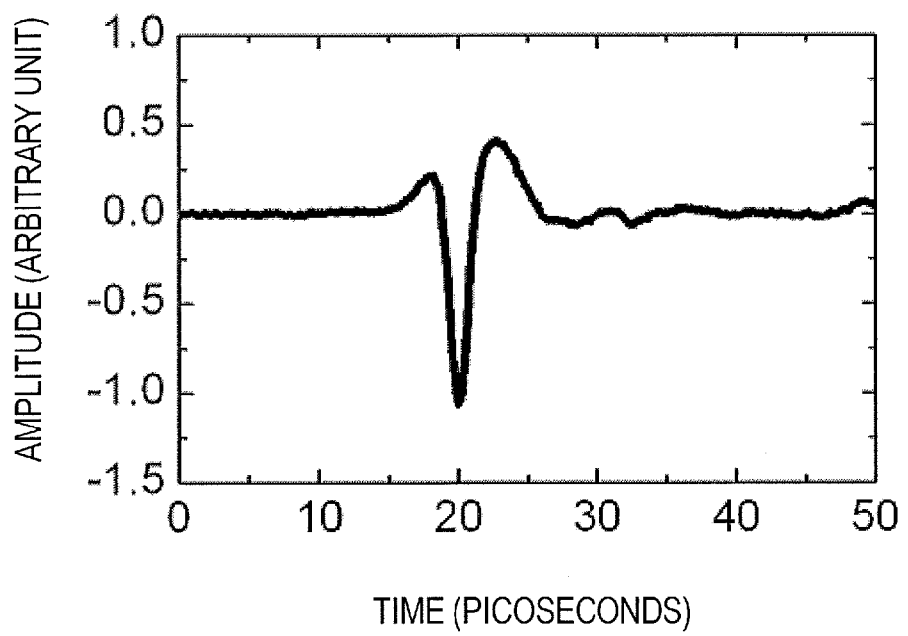
FIG. 10B is a graph showing the time domain waveform of a terahertz electromagnetic wave generated in such a situation where the terahertz electromagnetic wave generator comprised of $Bi_2O_3$ and $SiO_2$ was irradiated with a femtosecond laser beam and was arranged so that a left half of the area irradiated with the laser beam would be $Bi_2O_3$ and a right half of that area would be $SiO_2$.
Figure 11:
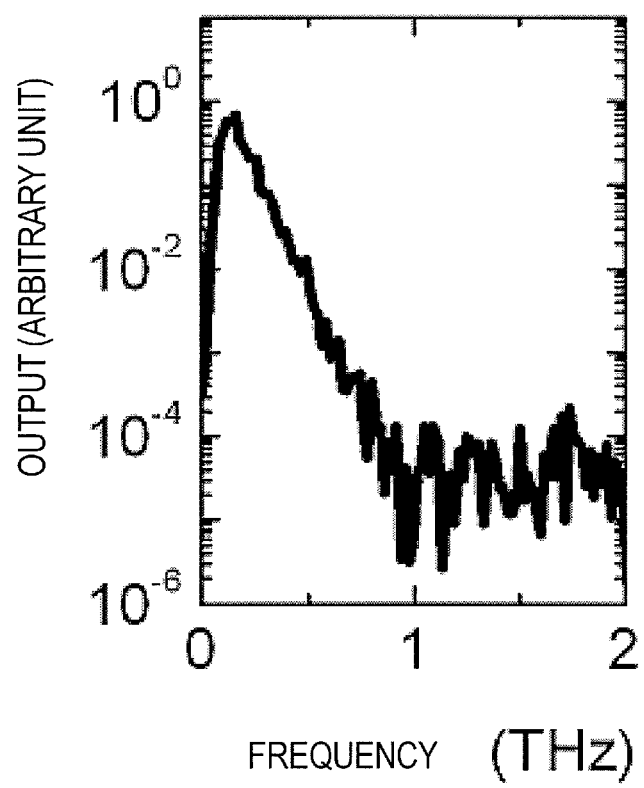
FIG. 11 is a graph showing the power spectrum of the terahertz electromagnetic wave shown in FIG. 10B.

Next, the terahertz electromagnetic wave generator was irradiated with the femtosecond laser beam so that a right half of the area irradiated with the laser beam would be $SiO_2$ and a left half of that area would be $Bi_2Te_3$ as shown in FIG. 10A. The time domain waveform of the terahertz electromagnetic wave generated in such a situation is shown in FIG. 10B. As can be seen from the time domain waveform of the terahertz electromagnetic wave shown in FIG. 10B, a pulse wave with a negative peak intensity was generated at around 20 ps. FIG. 11 shows a power spectrum obtained by subjecting this time domain waveform to a Fourier transform. The electromagnetic wave generated had a frequency range of about 0.1 THz to about 1 THz. Thus, it was confirmed that a terahertz electromagnetic wave had been generated.

As can be seen from these results, the electric field polarity of the terahertz electromagnetic wave (i.e., whether the maximum peak of the time waveform is positive or negative) inverted depending on whether the terahertz electromagnetic wave had been generated so that a right half of the area irradiated with the laser beam would be $Bi_2Te_3$ and a left half of that area would be $SiO_2$ as shown in FIG. 8A or that a right half of the area irradiated with the laser beam would be $SiO_2$ and a left half of that area would be $Bi_2Te_3$ as shown in FIG. 10A. The electric field polarity of the terahertz electromagnetic wave is determined by the direction of current to be its source. That is why if the electric field polarity of the terahertz electromagnetic wave observed in FIG. 8B was inverse of that of the terahertz electromagnetic wave observed in FIG. 10B, then it means that the direction of current to be induced changed depending on whether $Bi_2Te_3$ was located on the left half of the area irradiated with the laser beam or on the right half thereof. In fact, if the terahertz electromagnetic wave generator is irradiated with the femtosecond laser beam so that a left half of the area irradiated with the laser beam will be $Bi_2Te_3$ and a right half of that area will be $SiO_2$ as shown in FIG. 10A, holes heated within $Bi_2Te_3$ will diffuse to the left, and therefore, current will flow to the left. On the other hand, if the terahertz electromagnetic wave generator is irradiated with the femtosecond laser beam so that a left half of the area irradiated with the laser beam will be $SiO_2$ and a right half of that area will be $Bi_2Te_3$ as shown in FIG. 8A, holes heated within $Bi_2Te_3$ will diffuse to the right, and therefore, current will flow to the right. This behavior is opposite from that of Example 1 in which Bi was used as an n-type thermoelectric material, and indicates the difference in the type of carriers (i.e., whether the carriers are electrons or holes) between these two examples. Since $SiO_2$ is an insulator, no current will flow through $SiO_2$ due to thermal diffusion.

Thus it can be understood why the polarity of the terahertz electromagnetic wave observed in FIG. 8B was inverse of that of the terahertz electromagnetic wave observed in FIG. 10B. And it can also be seen that the current generated in $Bi_2Te_3$ that is a thermoelectric material becomes the source of a terahertz electromagnetic wave.

Figure 12:
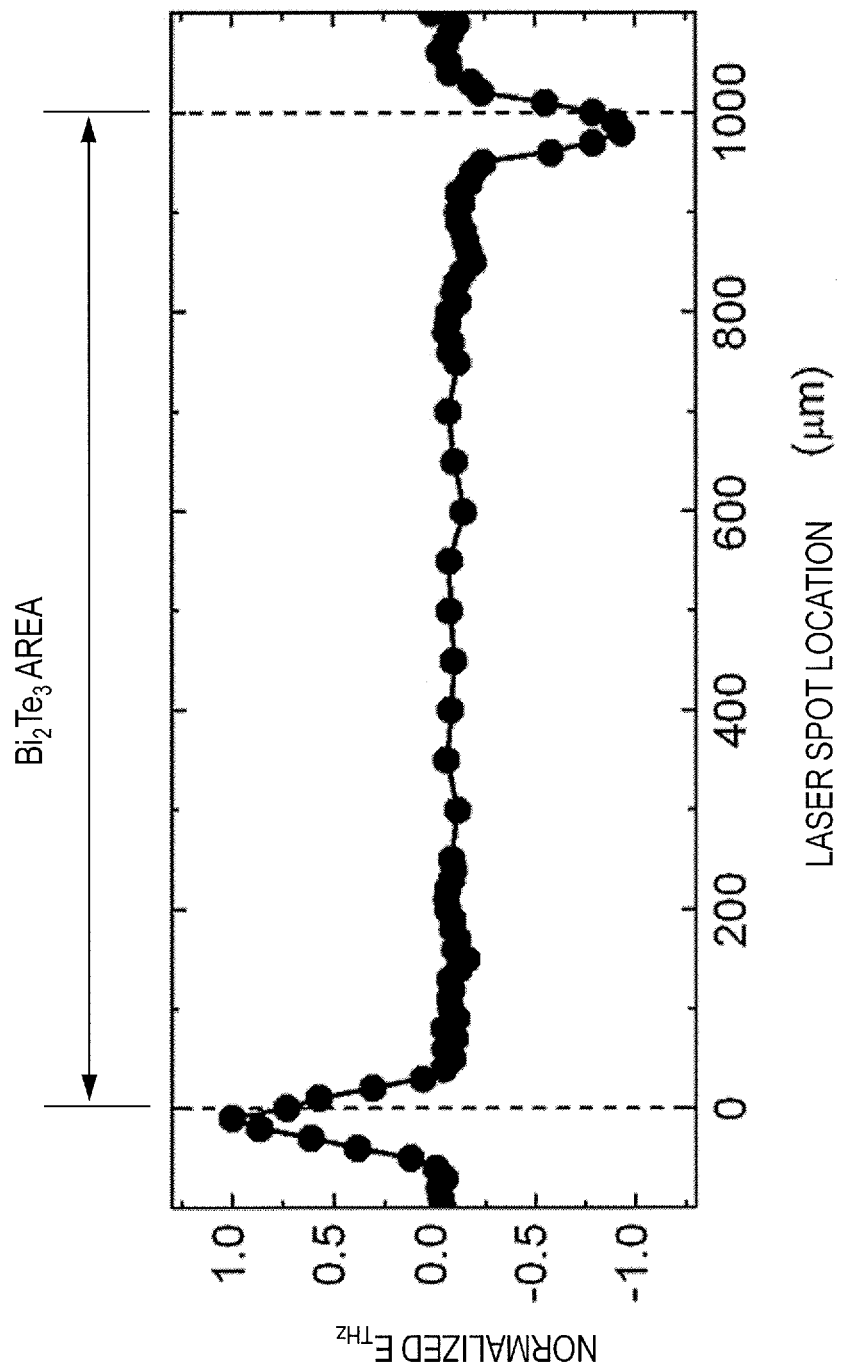
FIG. 12 is a graph showing a variation in the peak intensity of a terahertz electromagnetic wave that a terahertz electromagnetic wave generator comprised of $Bi_2O_3$ and $SiO_2$ generated when the area irradiated with a femtosecond laser beam was scanned one-dimensionally.

Next, a variation in the peak intensity of the terahertz electromagnetic wave generated was traced by scanning the area irradiated with the femtosecond laser beam from the $SiO_2$ side toward the $Bi_2Te_3$ side. In this case, the femtosecond laser beam had a beam diameter of 100 μm. The results are shown in FIG. 12. When the laser beam spot was located completely within the $SiO_2$ area, no terahertz electromagnetic wave was generated. However, when the laser beam was incident on an edge of the $Bi_2Te_3$ layer, the peak intensity of the terahertz electromagnetic wave started to rise. And when the center of the laser beam spot was located in the vicinity of an edge of the $Bi_2Te_3$ layer, the peak intensity of the terahertz electromagnetic wave reached its maximum value. As the laser beam spot was further shifted toward the $Bi_2Te_3$ side, the peak intensity of the terahertz electromagnetic wave started to decrease. And when the laser beam spot entered the $Bi_2Te_3$ area completely, no terahertz electromagnetic wave was observed anymore. However, when the laser beam spot was shifted to reach the opposite edge of the $Bi_2Te_3$ layer, a terahertz electromagnetic wave was observed again. These results reveal that to generate a terahertz electromagnetic wave, it is important that an edge of the thermoelectric material layer falls within the area irradiated with the laser beam.

The terahertz electromagnetic wave radiation properties of Bi and $Bi_2Te_3$ that have been described for Examples 1 and 2 exhibited no dependence on the polarization of the femtosecond laser beam. This indicates that the terahertz electromagnetic wave generating mechanism is not a secondary nonlinear effect. As for semiconductors and insulators, on the other hand, a so-called "photo-Dember effect" that is a terahertz electromagnetic wave generating mechanism which has something to do with diffusion of photo-excited carriers has also been reported. However, the polarity of a terahertz electromagnetic wave generated under the photo-Dember effect does not depend on the type of the majority carriers (i.e., whether the majority carriers are electrons or holes) (see Physical Review B73, 155330, (2006)), which is different from the terahertz electromagnetic wave radiation properties of Examples 1 and 2. Consequently, the terahertz electromagnetic wave generating mechanism of the present disclosure does not result from the photo-Dember effect.

As can be seen from the foregoing description, a method of generating a terahertz electromagnetic wave according to the present disclosure is based on a novel mechanism, and the present disclosure provides a simple terahertz electromagnetic wave source which needs no external voltage supply.

EXAMPLE 3

An element which used Bi as a thermoelectric material and $Al_2O_3$ as a substrate material, respectively, was fabricated by the following method. Bi is an n-type thermoelectric material and had a Seebeck coefficient of −75 μV/K and an electrical resistivity of 0.1 mΩcm. On the other hand, $Al_2O_3$ is an insulator, not a thermoelectric material.

The same measurement was made under the same condition as in Example 1.

Figure 13A:
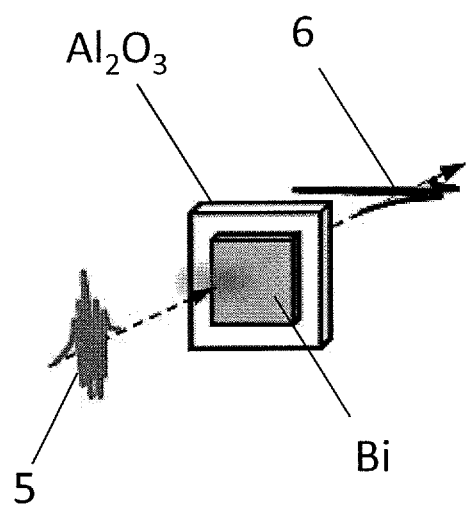
FIG. 13A is a perspective view illustrating a situation where a terahertz electromagnetic wave generator comprised of Bi and $Al_2O_3$ is arranged so that a right half of the area irradiated with a laser beam will be Bi and a left half of that area will be $Al_2O_3$.
Figure 13B:
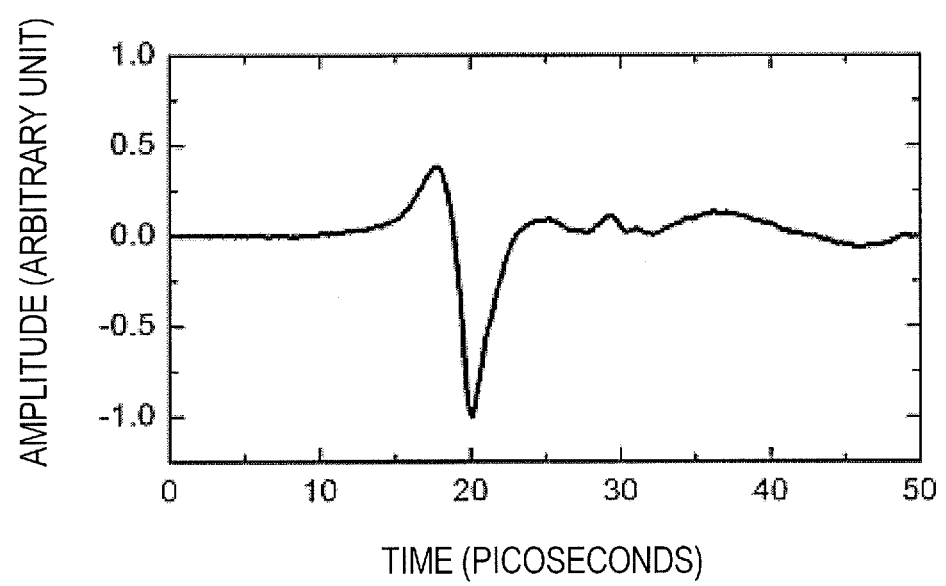
FIG. 13B is a graph showing the time domain waveform of a terahertz electromagnetic wave generated in such a situation where the terahertz electromagnetic wave generator comprised of Bi and $Al_2O_3$ was irradiated with a femtosecond laser beam and was arranged so that a right half of the area irradiated with the laser beam would be Bi and a left half of that area would be $Al_2O_3$.

First of all, the terahertz electromagnetic wave generator was irradiated with the femtosecond laser beam so that a right half of the area irradiated with the laser beam would be Bi and a left half of that area would be $Al_2O_3$ as shown in FIG. 13A. The time domain waveform of the terahertz electromagnetic wave generated in such a situation is shown in FIG. 13B. As can be seen from the time domain waveform of the terahertz electromagnetic wave shown in FIG. 13B, a pulse wave with a negative peak intensity was generated at around 20 ps.

Figure 14A:
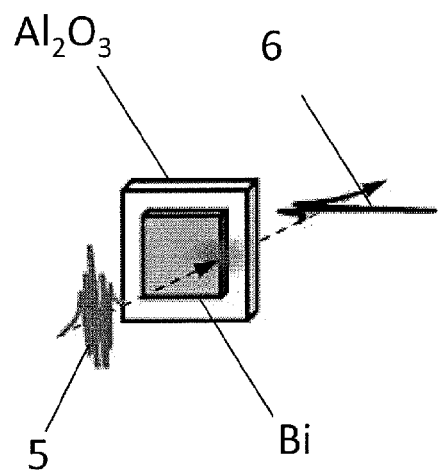
FIG. 14A is a perspective view illustrating a situation where a terahertz electromagnetic wave generator comprised of Bi and $Al_2O_3$ is arranged so that a left half of the area irradiated with a laser beam will be Bi and a right half of that area will be $Al_2O_3$.
Figure 14B:
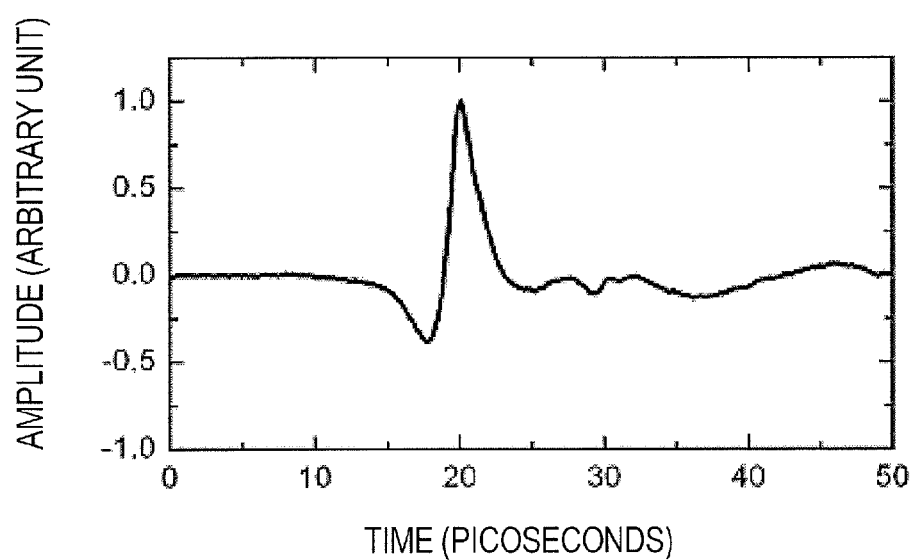
FIG. 14B is a graph showing the time domain waveform of a terahertz electromagnetic wave generated in such a situation where the terahertz electromagnetic wave generator comprised of Bi and $Al_2O_3$ was irradiated with a femtosecond laser beam and was arranged so that a left half of the area irradiated with the laser beam would be Bi and a right half of that area would be $Al_2O_3$.

Next, the terahertz electromagnetic wave generator was irradiated with the femtosecond laser beam so that a right half of the area irradiated with the laser beam would be $Al_2O_3$ and a left half of that area would be Bi as shown in FIG. 14A. The time domain waveform of the terahertz electromagnetic wave generated in such a situation is shown in FIG. 14B. As can be seen from the time domain waveform of the terahertz electromagnetic wave shown in FIG. 14B, a pulse wave with a positive peak intensity was generated at around 20 ps.

As in Example 1 described above, it can be understood why the polarity of the terahertz electromagnetic wave observed in FIG. 13B was inverse of that of the terahertz electromagnetic wave observed in FIG. 14B. And it can also be seen that even when $Al_2O_3$ was used as a substrate material, a terahertz electromagnetic wave was also generated on the same principle.

EXAMPLE 4

An element which used Bi as a thermoelectric material and MgO as a substrate material, respectively, was fabricated by the following method. Bi is an n-type thermoelectric material and had a Seebeck coefficient of −75 μV/K and an electrical resistivity of 0.1 mΩcm. On the other hand, MgO is an insulator, not a thermoelectric material.

The same measurement was made under the same condition as in Example 1.

Figure 15A:
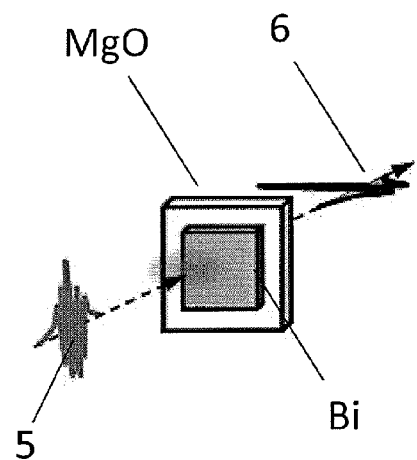
FIG. 15A is a perspective view illustrating a situation where a terahertz electromagnetic wave generator comprised of Bi and MgO is arranged so that a right half of the area irradiated with a laser beam will be Bi and a left half of that area will be MgO.
Figure 15B:
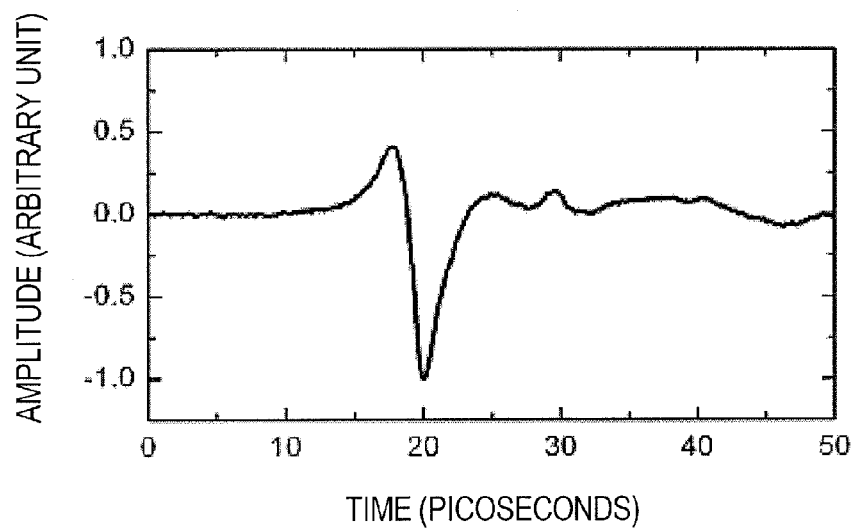
FIG. 15B is a graph showing the time domain waveform of a terahertz electromagnetic wave generated in such a situation where the terahertz electromagnetic wave generator comprised of Bi and MgO was irradiated with a femtosecond laser beam and was arranged so that a right half of the area irradiated with the laser beam would be Bi and a left half of that area would be MgO.

First of all, the terahertz electromagnetic wave generator was irradiated with the femtosecond laser beam so that a right half of the area irradiated with the laser beam would be Bi and a left half of that area would be MgO as shown in FIG. 15A. The time domain waveform of the terahertz electromagnetic wave generated in such a situation is shown in FIG. 15B. As can be seen from the time domain waveform of the terahertz electromagnetic wave shown in FIG. 15B, a pulse wave with a negative peak intensity was generated at around 20 ps.

Figure 16A:
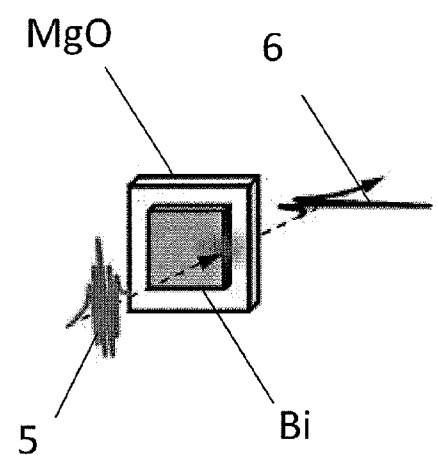
FIG. 16A is a perspective view illustrating a situation where a terahertz electromagnetic wave generator comprised of Bi and MgO is arranged so that a left half of the area irradiated with a laser beam will be Bi and a right half of that area will be MgO.
Figure 16B:
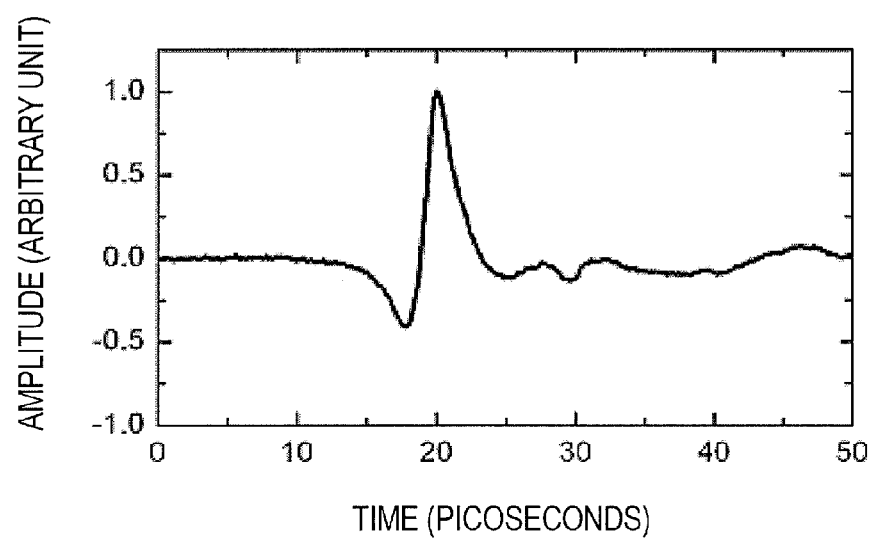
FIG. 16B is a graph showing the time domain waveform of a terahertz electromagnetic wave generated in such a situation where the terahertz electromagnetic wave generator comprised of Bi and MgO was irradiated with a femtosecond laser beam and was arranged so that a left half of the area irradiated with the laser beam would be Bi and a right half of that area would be MgO.

Next, the terahertz electromagnetic wave generator was irradiated with the femtosecond laser beam so that a right half of the area irradiated with the laser beam would be MgO and a left half of that area would be Bi as shown in FIG. 16A. The time domain waveform of the terahertz electromagnetic wave generated in such a situation is shown in FIG. 16B. As can be seen from the time domain waveform of the terahertz electromagnetic wave shown in FIG. 16B, a pulse wave with a positive peak intensity was generated at around 20 ps.

As in Example 1 described above, it can be understood why the polarity of the terahertz electromagnetic wave observed in FIG. 15B was inverse of that of the terahertz electromagnetic wave observed in FIG. 16B. And it can also be seen that even when MgO was used as a substrate material, a terahertz electromagnetic wave was also generated on the same principle.

EXAMPLE 5

An element which used p-type $Bi_2Te_3$ as a thermoelectric material and $Al_2O_3$ as a substrate material, respectively, was fabricated by the following method. $Bi_2Te_3$ had a Seebeck coefficient of +210 μV/K and an electrical resistivity of 1 mΩcm. On the other hand, $Al_2O_3$ is an insulator, not a thermoelectric material. The same measurement was made under the same condition as in Example 1.

Figure 17A:
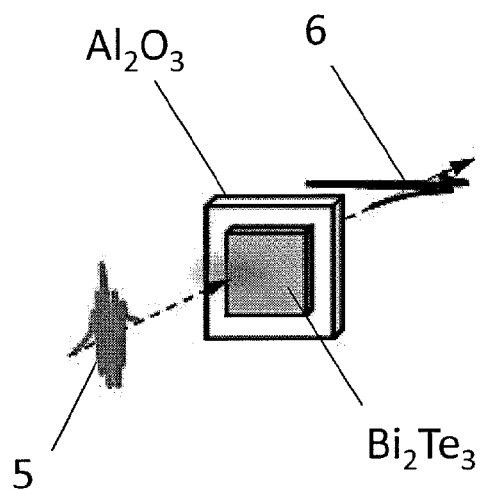
FIG. 17A is a perspective view illustrating a situation where a terahertz electromagnetic wave generator comprised of $Bi_2Te_3$ and $Al_2O_3$ is arranged so that a right half of the area irradiated with a laser beam will be $Bi_2Te_3$ and a left half of that area will be $Al_2O_3$.
Figure 17B:
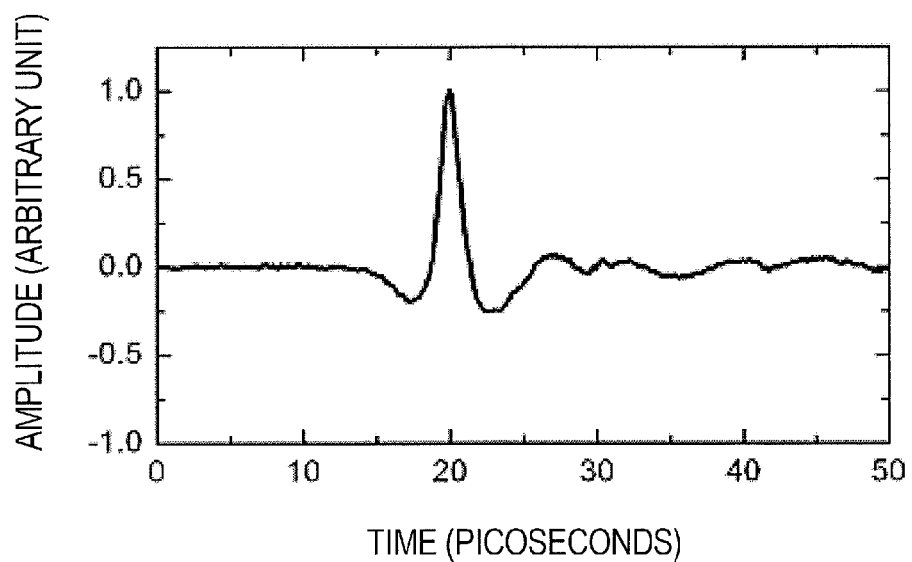
FIG. 17B is a graph showing the time domain waveform of a terahertz electromagnetic wave generated in such a situation where the terahertz electromagnetic wave generator comprised of $Bi_2Te_3$ and $Al_2O_3$ was irradiated with a femtosecond laser beam and was arranged so that a right half of the area irradiated with the laser beam would be $Bi_2Te_3$ and a left half of that area would be $Al_2O_3$.

First of all, the terahertz electromagnetic wave generator was irradiated with the femtosecond laser beam so that a right half of the area irradiated with the laser beam would be $Bi_2Te_3$ and a left half of that area would be $Al_2O_3$ as shown in FIG. 17A. The time domain waveform of the terahertz electromagnetic wave generated in such a situation is shown in FIG. 17B. As can be seen from the time domain waveform of the terahertz electromagnetic wave shown in FIG. 17B, a pulse wave with a positive peak intensity was generated at around 20 ps.

Figure 18A:
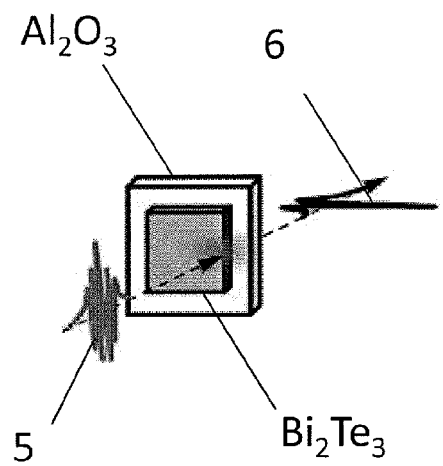
FIG. 18A is a perspective view illustrating a situation where a terahertz electromagnetic wave generator comprised of $Bi_2Te_3$ and $Al_2O_3$ is arranged so that a left half of the area irradiated with a laser beam will be $Bi_2Te_3$ and a right half of that area will be $Al_2O_3$.
Figure 18B:
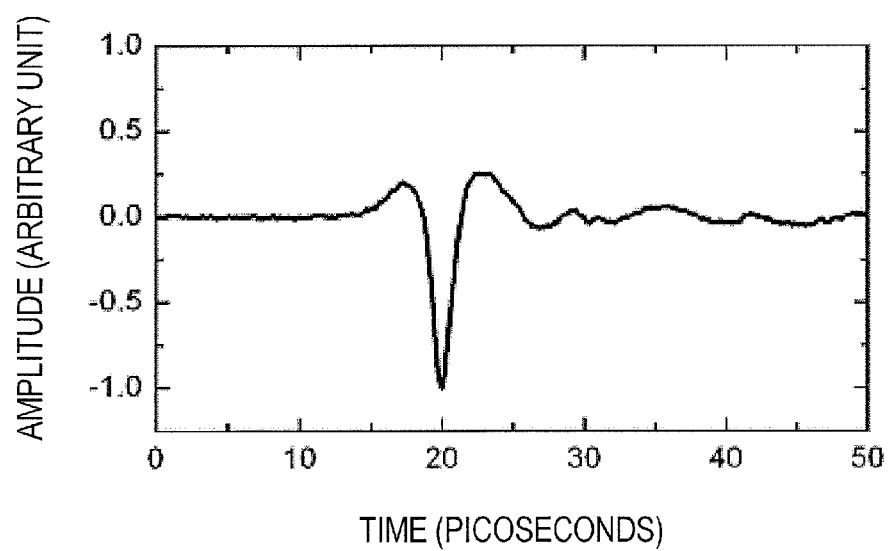
FIG. 18B is a graph showing the time domain waveform of a terahertz electromagnetic wave generated in such a situation where the terahertz electromagnetic wave generator comprised of $Bi_2Te_3$ and $Al_2O_3$ was irradiated with a femtosecond laser beam and was arranged so that a left half of the area irradiated with the laser beam would be $Bi_2Te_3$ and a right half of that area would be $Al_2O_3$.

Next, the terahertz electromagnetic wave generator was irradiated with the femtosecond laser beam so that a right half of the area irradiated with the laser beam would be $Al_2O_3$ and a left half of that area would be $Bi_2Te_3$ as shown in FIG. 18A. The time domain waveform of the terahertz electromagnetic wave generated in such a situation is shown in FIG. 18B. As can be seen from the time domain waveform of the terahertz electromagnetic wave shown in FIG. 18B, a pulse wave with a negative peak intensity was generated at around 20 ps.

As in Example 4 described above, it can be understood why the polarity of the terahertz electromagnetic wave observed in FIG. 17B was inverse of that of the terahertz electromagnetic wave observed in FIG. 18B. And it can also be seen that even when $Al_2O_3$ was used as a substrate material, a terahertz electromagnetic wave was also generated on the same principle.

EXAMPLE 6

An element which used p-type $Bi_2Te_3$ as a thermoelectric material and MgO as a substrate material, respectively, was fabricated by the following method. $Bi_2Te_3$ had a Seebeck coefficient of +210 μV/K and an electrical resistivity of 1 mΩcm. On the other hand, MgO is an insulator, not a thermoelectric material. The same measurement was made under the same condition as in Example 1.

Figure 19A:
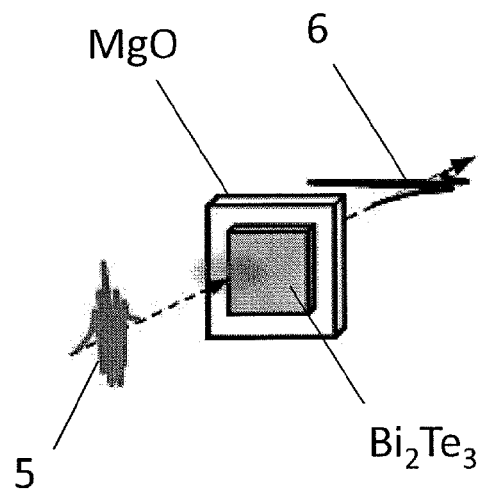
FIG. 19A is a perspective view illustrating a situation where a terahertz electromagnetic wave generator comprised of $Bi_2Te_3$ and MgO is arranged so that a right half of the area irradiated with a laser beam will be $Bi_2Te_3$ and a left half of that area will be MgO.
Figure 19B:
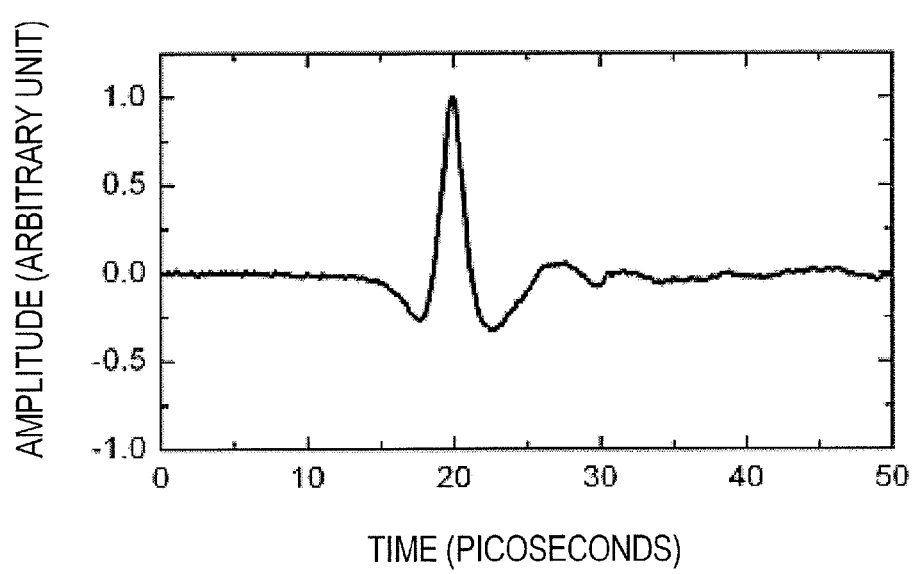
FIG. 19B is a graph showing the time domain waveform of a terahertz electromagnetic wave generated in such a situation where the terahertz electromagnetic wave generator comprised of $Bi_2Te_3$ and MgO was irradiated with a femtosecond laser beam and was arranged so that a right half of the area irradiated with the laser beam would be $Bi_2Te_3$ and a left half of that area would be MgO.

First of all, the terahertz electromagnetic wave generator was irradiated with the femtosecond laser beam so that a right half of the area irradiated with the laser beam would be $Bi_2Te_3$ and a left half of that area would be MgO as shown in FIG. 19A. The time domain waveform of the terahertz electromagnetic wave generated in such a situation is shown in FIG. 19B. As can be seen from the time domain waveform of the terahertz electromagnetic wave shown in FIG. 19B, a pulse wave with a positive peak intensity was generated at around 20 ps.

Figure 20A:
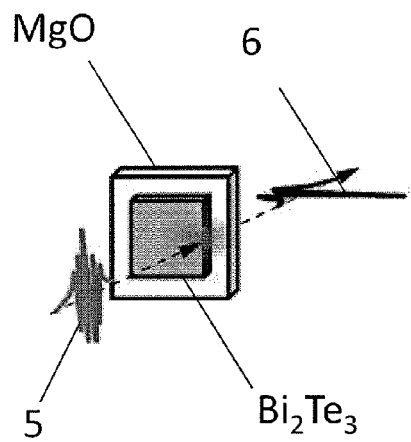
FIG. 20A is a perspective view illustrating a situation where a terahertz electromagnetic wave generator comprised of $Bi_2Te_3$ and MgO is arranged so that a left half of the area irradiated with a laser beam will be $Bi_2Te_3$ and a right half of that area will be MgO.
Figure 20B:
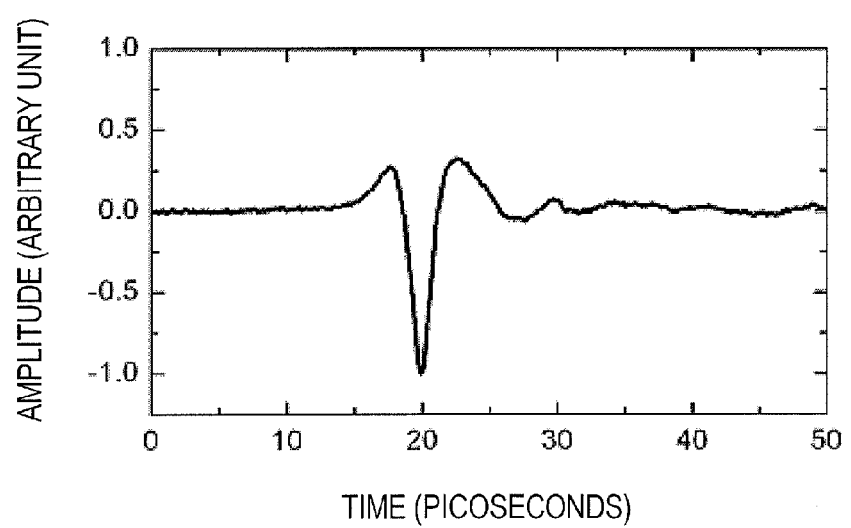
FIG. 20B is a graph showing the time domain waveform of a terahertz electromagnetic wave generated in such a situation where the terahertz electromagnetic wave generator comprised of $Bi_2Te_3$ and MgO was irradiated with a femtosecond laser beam and was arranged so that a left half of the area irradiated with the laser beam would be $Bi_2Te_3$ and a right half of that area would be MgO.

Next, the terahertz electromagnetic wave generator was irradiated with the femtosecond laser beam so that a right half of the area irradiated with the laser beam would be MgO and a left half of that area would be $Bi_2Te_3$ as shown in FIG. 20A. The time domain waveform of the terahertz electromagnetic wave generated in such a situation is shown in FIG. 20B. As can be seen from the time domain waveform of the terahertz electromagnetic wave shown in FIG. 20B, a pulse wave with a negative peak intensity was generated at around 20 ps.

As in Example 4 described above, it can be understood why the polarity of the terahertz electromagnetic wave observed in FIG. 19B was inverse of that of the terahertz electromagnetic wave observed in FIG. 20B. And it can also be seen that even when MgO was used as a substrate material, a terahertz electromagnetic wave was also generated on the same principle.

COMPARATIVE EXAMPLE 1

As a comparative example, the same experiment was carried out on Au which is not a thermoelectric material (and which had a Seebeck coefficient of +2 μV/K and an electrical resistivity of 0.002 mΩcm).

An Au layer was deposited by evaporation process to a thickness of 50 nm on an $SiO_2$ substrate (10 mm×10 mm×0.5 mm). The evaporation process was carried out without heating the $SiO_2$ substrate after the film deposition chamber had been evacuated to a pressure of $1.0 \times 10^{-3}$ Pa or less. When the Au layer was deposited, the principal surface of the $SiO_2$ substrate was covered with a metallic mask so that only a portion of the principal surface of the $SiO_2$ substrate would be coated with the Au layer. While the $SiO_2$ substrate had an area of 10 mm×10 mm, the Au layer deposited on the substrate had an area of 1 mm×1 mm.

As a femtosecond laser diode to heat the terahertz electromagnetic wave generator, a Ti: Sapphire laser diode with a wavelength of 800 nm, a pulse width of 100 fs and a pulse rate of 80 MHz was used.

With respect to the terahertz electromagnetic wave generator thus fabricated, one edge of the Au layer was irradiated with a femtosecond laser beam that had been condensed to 100 μm (=2r), thereby measuring the time domain waveform of the terahertz electromagnetic wave. In this case, adjustment was made so that the center of the laser beam would be located on one edge of the Au layer.

Figure 21A:
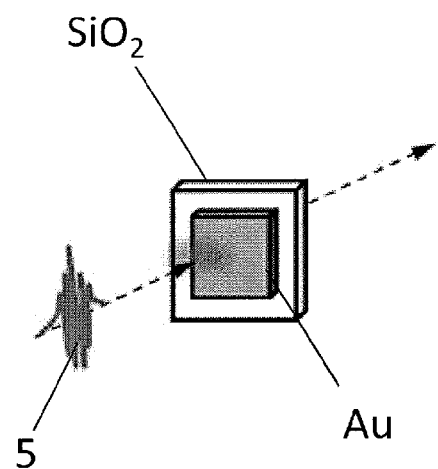
FIG. 21A is a perspective view illustrating a situation where a terahertz electromagnetic wave generator comprised of Au and $SiO_2$ is arranged so that a right half of the area irradiated with a laser beam will be Au and a left half of that area will be $SiO_2$.
Figure 21B:
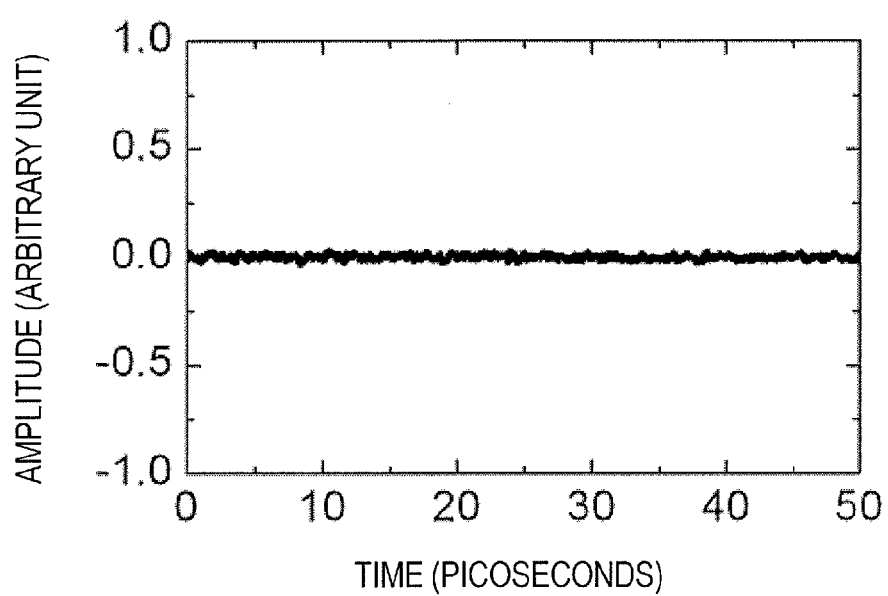
FIG. 21B is a graph showing the time domain waveform of a terahertz electromagnetic wave generated in such a situation where the terahertz electromagnetic wave generator comprised of Au and $SiO_2$ was irradiated with a femtosecond laser beam and was arranged so that a right half of the area irradiated with the laser beam would be Au and a left half of that area would be $SiO_2$.

First of all, the terahertz electromagnetic wave generator was irradiated with the femtosecond laser beam so that a right half of the area irradiated with the laser beam would be Au and a left half of that area would be $SiO_2$ as shown in FIG. 21A. The time domain waveform of the electromagnetic wave generated in such a situation is shown in FIG. 21B. As can be seen from the time domain waveform of the electromagnetic wave shown in FIG. 21B, there was nothing but noise with no definite peaks observed, and no terahertz electromagnetic wave had been generated.

Figure 22A:
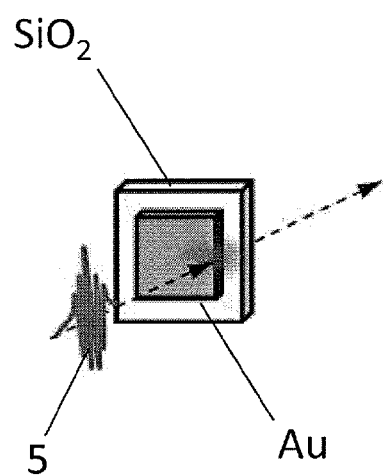
FIG. 22A is a perspective view illustrating a situation where a terahertz electromagnetic wave generator comprised of Au and $SiO_2$ is arranged so that a left half of the area irradiated with a laser beam will be Au and a right half of that area will be $SiO_2$.
Figure 22B:
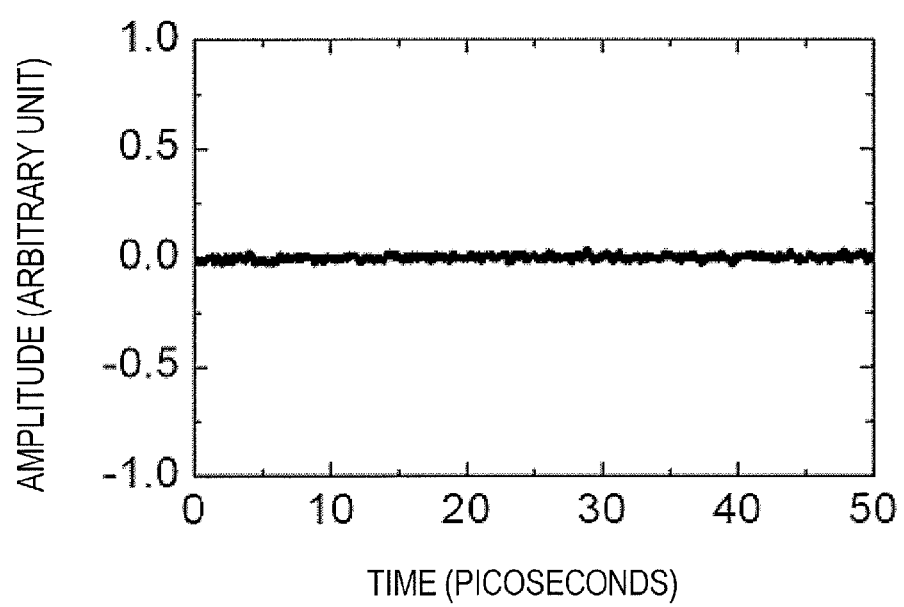
FIG. 22B is a graph showing the time domain waveform of a terahertz electromagnetic wave generated in such a situation where the terahertz electromagnetic wave generator comprised of Au and $SiO_2$ was irradiated with a femtosecond laser beam and was arranged so that a left half of the area irradiated with the laser beam would be Au and a right half of that area would be $SiO_2$.

Next, the terahertz electromagnetic wave generator was irradiated with the femtosecond laser beam so that a right half of the area irradiated with the laser beam would be $SiO_2$ and a left half of that area would be Au as shown in FIG. 22A. The time domain waveform of the electromagnetic wave generated in such a situation is shown in FIG. 22B. As can be seen from the time domain waveform of the electromagnetic wave shown in FIG. 22B, there was nothing but noise with no definite peaks observed, and no terahertz electromagnetic wave had been generated.

Thus, the present inventors discovered that no terahertz electromagnetic wave could be generated even if the element of the present disclosure was made of Au that is not a thermoelectric material defined herein, because Au certainly has low electrical resistivity but its Seebeck coefficient is also low.

COMPARATIVE EXAMPLE 2

As a comparative example, the same experiment was carried out on $Fe_2O_3$ which is not a thermoelectric material (and which had a Seebeck coefficient of −300 μV/K and an electrical resistivity of $10^5$ mΩcm).

An $Fe_2O_3$ layer was deposited by evaporation process to a thickness of 50 nm on an $Al_2O_3$ substrate (10 mm×10 mm×0.5 mm). The evaporation process was carried out without heating the $Al_2O_3$ substrate after the film deposition chamber had been evacuated to a pressure of $1.0 \times 10^{-3}$ Pa or less. When the $Fe_2O_3$ layer was deposited, the principal surface of the $Al_2O_3$ substrate was covered with a metallic mask so that only a portion of the principal surface of the $Al_2O_3$ substrate would be coated with the $Fe_2O_3$ layer. While the $Al_2O_3$ substrate had an area of 10 mm×10 mm, the $Fe_2O_3$ layer deposited on the substrate had an area of 1 mm×1 mm.

As a femtosecond laser diode to heat the terahertz electromagnetic wave generator, a Ti: Sapphire laser diode with a wavelength of 800 nm, a pulse width of 100 fs and a pulse rate of 80 MHz was used.

With respect to the terahertz electromagnetic wave generator thus fabricated, one edge of the $Fe_2O_3$ layer was irradiated with a femtosecond laser beam that had been condensed to 100 μm (=2r), thereby measuring the time domain waveform of the terahertz electromagnetic wave. In this case, adjustment was made so that the center of the laser beam would be located on one edge of the $Fe_2O_3$ layer and $Al_2O_3$.

Figure 23A:
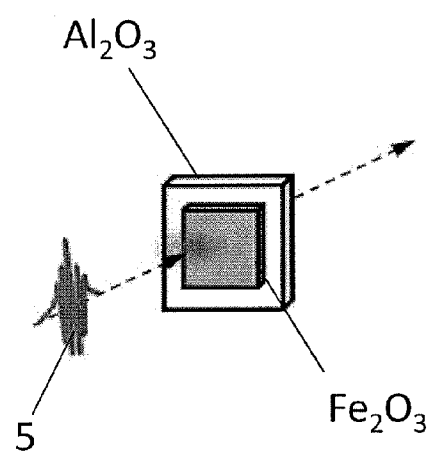
FIG. 23A is a perspective view illustrating a situation where a terahertz electromagnetic wave generator comprised of $Fe_2O_3$ and $Al_2O_3$ is arranged so that a right half of the area irradiated with a laser beam will be $Fe_2O_3$ and a left half of that area will be $Al_2O_3$.
Figure 23B:
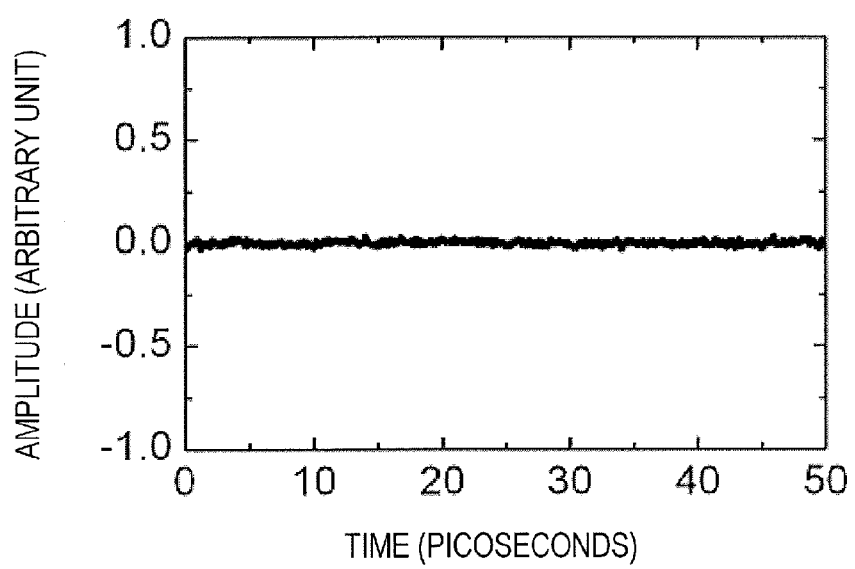
FIG. 23B is a graph showing the time domain waveform of a terahertz electromagnetic wave generated in such a situation where the terahertz electromagnetic wave generator comprised of $Fe_2O_3$ and $Al_2O_3$ was irradiated with a femtosecond laser beam and was arranged so that a right half of the area irradiated with the laser beam would be $Fe_2O_3$ and a left half of that area would be $Al_2O_3$.

First of all, the terahertz electromagnetic wave generator was irradiated with the femtosecond laser beam so that a right half of the area irradiated with the laser beam would be $Fe_2O_3$ and a left half of that area would be $Al_2O_3$ as shown in FIG. 23A. The time domain waveform of the electromagnetic wave generated in such a situation is shown in FIG. 23B. As can be seen from the time domain waveform of the electromagnetic wave shown in FIG. 23B, there was nothing but noise with no definite peaks observed, and no terahertz electromagnetic wave had been generated.

Figure 24A:
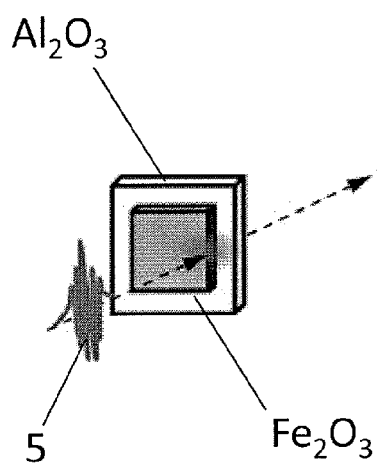
FIG. 24A is a perspective view illustrating a situation where a terahertz electromagnetic wave generator comprised of $Fe_2O_3$ and $Al_2O_3$ is arranged so that a left half of the area irradiated with a laser beam will be $Fe_2O_3$ and a right half of that area will be $Al_2O_3$.
Figure 24B:
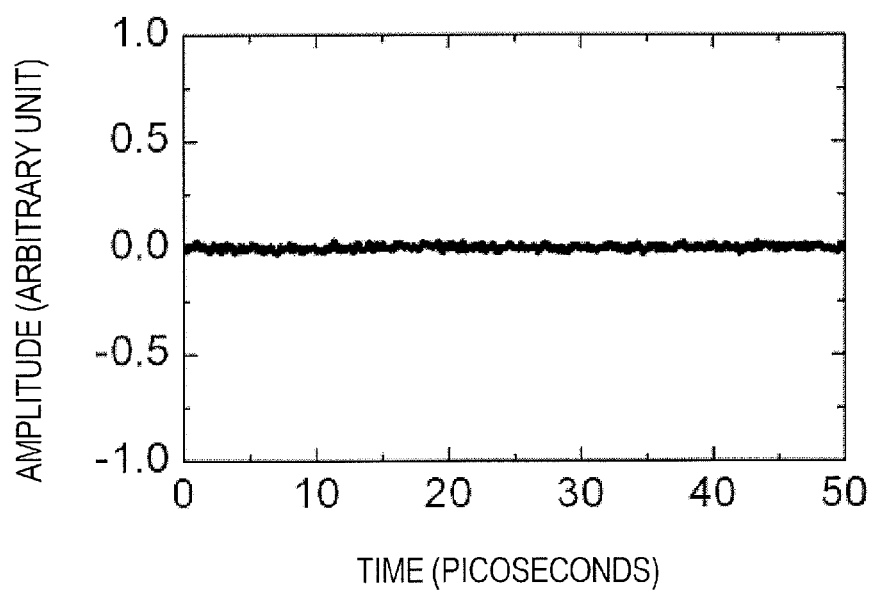
FIG. 24B is a graph showing the time domain waveform of a terahertz electromagnetic wave generated in such a situation where the terahertz electromagnetic wave generator comprised of $Fe_2O_3$ and $Al_2O_3$ was irradiated with a femtosecond laser beam and was arranged so that a left half of the area irradiated with the laser beam would be $Fe_2O_3$ and a right half of that area would be $Al_2O_3$.

Next, the terahertz electromagnetic wave generator was irradiated with the femtosecond laser beam so that a right half of the area irradiated with the laser beam would be $Al_2O_3$ and a left half of that area would be $Fe_2O_3$ as shown in FIG. 24A. The time domain waveform of the electromagnetic wave generated in such a situation is shown in FIG. 24B. As can be seen from the time domain waveform of the electromagnetic wave shown in FIG. 24B, there was nothing but noise with no definite peaks observed, and no terahertz electromagnetic wave had been generated.

Thus, the present inventors discovered that no terahertz electromagnetic wave could be generated even if the element of the present disclosure was made of $Fe_2O_3$ that is not a thermoelectric material defined herein, because $Fe_2O_3$ certainly has a high Seebeck coefficient but its electrical resistivity is also high.

In the examples described above, the thermoelectric material layer is supposed to be irradiated with the femtosecond laser beam so that its beam spot crosses an edge of the surface of the thermoelectric material layer on the right- or left-hand side (i.e., an edge X which runs parallel to the Y axis of an XY plane). However, this is just an example and the laser beam spot does not always have to be formed there. Alternatively, the laser beam spot may also be formed across an upper or lower edge of the surface of the thermoelectric material layer (i.e., an edge which runs parallel to the X axis of the XY plane), for example. Also, since the thermoelectric material layer may be patterned into any arbitrary shape, the location and direction of the edge do not have to be the exemplary ones of the examples described above, either.

Also, in the examples described above, the thickness of the thermoelectric material layer is set to be 50 nm to make the comparison easily. However, it would be obvious to those skilled in the art from the entire disclosure of the present application that even if the thickness of the thermoelectric material layer is not 50 nm but falls within the range of 10 nm to 1000 nm (=1 μm), for example, similar effects will also be achieved.

Furthermore, as can be seen easily from the principle of generating a terahertz electromagnetic wave that has already been described in the foregoing description of the present disclosure, respective materials for the thermoelectric material layer and substrate according to the present disclosure do not have to be the ones used in the examples described above, but any of a wide variety of thermoelectric materials and substrate materials may be used in an arbitrary combination.

With the technique of generating a terahertz electromagnetic wave according to the present disclosure, a terahertz electromagnetic wave can be generated by using a simpler configuration than conventional ones without providing any external voltage supply. Thus, the present disclosure is applicable to not only evaluation of the properties of various kinds of materials, but also security, healthcare and numerous other fields, using a terahertz electromagnetic wave.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A terahertz electromagnetic wave generator comprising:
a substrate;
a thermoelectric material layer supported by the substrate, the thermoelectric material layer having a surface; and
a pulsed laser light source system configured to irradiate an edge of the surface of the thermoelectric material layer with pulsed light to locally heat the thermoelectric material layer, thereby generating a terahertz electromagnetic wave from the thermoelectric material layer.

2. The terahertz electromagnetic wave generator of claim 1, wherein the pulsed laser light source system is configured to form a light spot which crosses the edge of the surface of the thermoelectric material layer.

3. The terahertz electromagnetic wave generator of claim 1, wherein the terahertz electromagnetic wave has a frequency falling within the range of 0.1 THz to 100 THz.

4. The terahertz electromagnetic wave generator of claim 3, wherein the pulsed laser light source system comprises:
- a light source which emits the pulsed light, of which the pulse width falls within the range of 1 femtosecond to 1 nanosecond; and
- an optical system which guides the pulsed light that is emitted from the light source toward the edge of the surface of the thermoelectric material layer.

5. The terahertz electromagnetic wave generator of claim 4, wherein the light source is a femtosecond laser light source.

6. The terahertz electromagnetic wave generator of claim 1, wherein the thermoelectric material layer is made of a material selected from the group consisting of a single-element thermoelectric material, an alloy-based thermoelectric material, and an oxide-based thermoelectric material.

7. The terahertz electromagnetic wave generator of claim 6, wherein the thermoelectric material layer is made of at least one material selected from the group consisting of Bi, Sb, a BiTe-based alloy, a PbTe-based alloy, an SiGe-based alloy, $Ca_xCoO_2$, $Na_xCoO_2$, and $SrTiO_3$.

8. The terahertz electromagnetic wave generator of claim 1, wherein the thermoelectric material layer has a thickness of 10 nm to 1 μm.

9. The terahertz electromagnetic wave generator of claim 1, wherein the substrate is configured to transmit the terahertz electromagnetic wave.

10. A terahertz spectrometer comprising:
- the terahertz electromagnetic wave generator of claim 1;
- an optical system which irradiates an object with a terahertz electromagnetic wave that is generated by the terahertz electromagnetic wave generator; and
- a detector which detects the terahertz electromagnetic wave that is transmitted through, or reflected from, the object.

11. The terahertz spectrometer of claim 10, further comprising a processing apparatus which generates an image representing a terahertz electromagnetic wave with a particular wavelength based on the output of the detector.

12. A method of generating a terahertz electromagnetic wave, the method comprising:
- (A) providing a thermoelectric material body; and
- (B) locally heating the thermoelectric material body by irradiating a portion of the thermoelectric material body with pulsed light, the step (B) comprising:
locally heating the thermoelectric material body so that an asymmetric heat distribution is formed in the thermoelectric material body; and
producing thermal diffusion current in the portion of the thermoelectric material body that is heated locally, thereby generating a terahertz electromagnetic wave.

* * * * *